United States Patent [19]

Sloan

[11] Patent Number: 4,975,433
[45] Date of Patent: Dec. 4, 1990

[54] AMINOMETHYL DERIVATIVES OF BIOLOGICALLY ACTIVE SUBSTANCES AND ENHANCED DELIVERY THEREOF ACROSS TOPICAL MEMBRANES

[75] Inventor: Kenneth B. Sloan, Gainesville, Fla.

[73] Assignee: University of Florida, Gainesville, Fla.

[21] Appl. No.: 304,272

[22] Filed: Jan. 31, 1989

Related U.S. Application Data

[60] Division of Ser. No. 906,468, Sep. 12, 1986, Pat. No. 4,845,081, which is a continuation-in-part of Ser. No. 662,055, Oct. 18, 1984, abandoned.

[51] Int. Cl.$^5$ ............... A61K 31/505; A61K 31/555; C07D 239/47
[52] U.S. Cl. .................................. 514/274; 514/184; 514/252; 544/64; 544/82; 544/123; 544/295; 544/317
[58] Field of Search ............... 544/317, 82, 123, 295, 544/64; 514/274, 232.2, 235.8, 252, 184

[56] References Cited

PUBLICATIONS

Kenneth B. Sloan et al., Tetrahedron, vol. 40, No. 20, pp. 3997–4001 (1984).

Primary Examiner—Mary C. Lee
Assistant Examiner—M. S. Howard
Attorney, Agent, or Firm—Kerkam, Stowell, Kondracki & Clarke

[57] ABSTRACT

A compound of the formula:

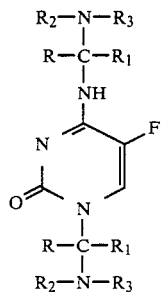

wherein:

R and $R_1$ may be the same or different and are selected from the group consisting of H; cycloalkyl groups having up to 10 carbon atoms; or straight or branched chain alkyl, alkenyl or alkynyl of 1 to 10 carbon atoms;

$R_2$ and $R_3$ together with the nitrogen atom to which they are bonded form a pyrrolidine, piperidine, N-methyl piperazine, piperazine or morpholine ring;

or a non-toxic pharmaceutically acceptable salt, adduct, oxide or other derivative thereof; and pharmaceutical compositions adapted for topical administration to a human or non-human animal and methods of topically administering the compositions to humans and non-human animals.

6 Claims, No Drawings

AMINOMETHYL DERIVATIVES OF BIOLOGICALLY ACTIVE SUBSTANCES AND ENHANCED DELIVERY THEREOF ACROSS TOPICAL MEMBRANES

RELATED APPLICATIONS

This is a Divisional of application Ser. No. 906,468, filed Sept. 12, 1986, now U.S. Pat. No. 4,845,081, which is a CIP of Ser. No. 662,055, filed Oct. 18, 1984, abandoned.

BACKGROUND OF THE INVENTION

1. Field of the Invention

The invention relates to certain aminomethyl derivatives of biologically active organic compounds useful as active ingredients in pharmaceutical compositions and methods of treatment.

2. The Prior Art

Intensive efforts have been undertaken recently in the area of enhancing the transport or delivery of drugs across such internal biological membranes as the bloodbarrier, blood-testis barrier, etc. The functional barriers of the endothelial brain capillary wall (bloodbrain barrier) and the seminiferous tubule capillary wall (blood-testis barrier) seriously limit the transport or delivery of biologically active drug species to the brain and testis, respectively.

Prodrugs comprising derivatized or otherwise chemical and/or physically modified forms of the drug species have been designed which more readily penetrate these barriers. Upon transport across the membrane they are converted in situ to the active form whereupon they perform their intended biological function in the target organ. These prodrugs are also designed to resist metabolic conversions and other forms of degradation until they have crossed the barrier.

Considerable research has also been conducted in an attempt to solve the problem of enhancing the delivery of topically applied drugs across the topical skin membrane.

Many drugs have been found to be useful for the treatment of various skin disease states such as psoriasis and atopic dermatitis when they are given orally but are not effective when applied topically. However, the use of a drug in a topical manner to treat a topical disease state is desirable in that only a locally effective concentration of the drug needs to be attained in the skin. On the other hand, an oral dose develops a systemic (whole body) concentration of the drug. For example, 6-mercaptopurine (6-MP) is orally effective in the treatment of psoriasis but it is not effective topically. The oral dose of 6-MP is 150-250 mg/day, and, assuming complete absorption, produces a whole body burden of 6-MP of 150-250 mg/day. However, the skin, which is the site of the disease, comprises only 5% of the body and the psoriasis may involve only 10-20% of the skin. Thus, assuming uniform distribution of the drug from the oral dose, the topical dose would only have to be 1% to 0.5% of the oral dose. The net result of being able to deliver 1% to 0.5% of the oral dose locally (i.e., topically, at the site where its action is needed) would result in a tremendous decrease in the systemic toxicity associated with the use of the drug to treat psoriasis.

Although there are a large number of drugs that fall into the category described above, there are also a large number of drugs that are either marginally effective topically or else they are used in formulations that are irritating because of the incorporation into the formulation of so-called penetration enhancers and solubilizers. These marginally effective drugs would benefit from a transient chemical modification that would increase their solubility in milder, more acceptable (by the patient) formulations and would increase the partitioning of the drug (prodrug) into the skin. An example of such a drug is 5-fluorouracil (5-FU) which is conventionally used in a formulation containing propylene glycol (a solubilizer) and a penetration enhancer. The propylene glycol is very irritating to the skin and the course of treatment may last for several weeks.

Polar, high-melting, heterocyclic drugs which are relatively insoluble in lipids and in water have presented a challenge to pharmaceutical chemists for some time in their efforts to improve the topical (or oral) delivery of such agents so that they can be used effectively in clinical situations. One approach to meeting this challenge has been to use N-acyloxyalkyl prodrug derivatives which are lower-melting and more lipophilic than the parent drugs. Recently, a number of examples of the application of this approach to modifying heterocyclic drugs have been described (Bodor et al, U.S. Pat. No. 4,061,753; CA 87, 152278 (1977) and Sloan et al, Int. J. Pharm., 12, 299–313 (1982); Stella et al, U.S. Pat. No. 4,163,058; CA 91, 193312 (1979); Ozaki et al, U.S. Pat. No. 4,267,326; Mollgaard et al, Int. J. Pharm. 12, 153–162 (1982) and Sloan et al, J. Pharm. Sci., 72, 372–378 (1983).

Although no examples of prodrugs have been reported where both water and lipid solubility have been optimized in order to obtain enhanced delivery of drugs across topical membranes, there are a number of prodrugs which incorporate an amino group into the derivative and exhibit enhanced lipid solubility and dermal delivery (Sloan, U.S. Pat. No. 4,206,220; CA 93, 8017 (1980); Sloan and Little, CA, 96, 104087 (1982); Sloan, CA, 97, 144855 (1982) and Bodor et al, Int. J. Pharm. 10, 307–321 (1982).

Although the topical membrane or skin is a "biological membrane", it differs substantially from other membranes in that the barrier to absorption of drugs is the stratum corneum which comprises a dead, dry (5–10% $H_2O$), compact keratin-containing material. All other biological membranes comprise live, essentially aqueous (75–80% $H_2O$) material. Obviously, therefore, the considerations bearing on the live transport or delivery of drug species across other biological membranes are altogether different from those bearing on the delivery of drugs across the topical skin membrane.

A high degree of liphophilicity is necessary in any prodrug designed to effectively cross the skin membrane. The prodrug must substantially immediately convert to the parent active drug species after transport across the stratum corneum, however.

It has been suggested heretofore to employ certain N-Mannich type bases (referred to herein as aminomethyl derivatives) as prodrugs for oral or parenteral administration. See, for example, Pitman, Med. Res. Rev., Vol. 1, No. 2, pp. 189–214 (1981); Johansen et al, Arch. Pharm. Chemi., Sci. Ed. 8, 141–151, 207–214 (1980); Johansen et al, Arch. Pharm. Chemi. Sci. Ed. 10, 111–121 (1982); Bundgaard et al, Int. J. Pharm. 7, 119–127, 129–136 (1980); Bundgaard et al, J. Pharm. Sci., 69, No.1, 44–47 (1980); Bundgaard et al, Acta. Pharm., Suec. 18, 129–134 (1981); Bundgaard et al, Int. J. Pharm., 9, 7–16 (1981); Bundgaard et al, Int. J.

Pharm., 8, 183-192 (1981); Bundgaard et al, Int. J. Pharm., 9, 7-16 (1981). There is no suggestion in the prior art, however, as to the utilization of such N-Mannich bases as topical prodrugs.

There is disclosed in U.S. Pat. No. 4,412,994 the use of Mannich-base hydroxamic acid prodrugs for topical administration to warm-blooded animals. The parent drugs from which the prodrugs are derived, however, are limited to "acyl residues of non-steroidal anti-inflammatory agents containing a carboxylic acid function".

The use of Mannich bases or aminomethyl derivatives for topical delivery involves the intact prodrug partitioning from a non-protic solvent (in which it is stable) into the skin (in which it is not stable because of the presence of water) where it reverts to the parent compound. On the other hand, the use of Mannich bases or aminomethyl derivatives for oral or parenteral use takes advantage of increased water solubility and increased dissolution properties of the derivatives to enhance the bioavilability of the parent drug, but it is the parent drug and not the prodrug that is actually involved in the partitioning from the aqueous environment (in which the prodrug is not stable) into the membranes and from there ultimately the systemic circulation. Thus, the topical delivery depends on the superior partioning properties of the intact prodrug while the oral or parenteral delivery still depends on partitioning properties of the parent drug and gains its only advantage from the more immediate and higher solution concentrations of the parent drug that develop from the use of the prodrugs.

It is an object of the present invention to provide novel aminomethyl derivatives of a class of biologically active organic compounds which function in a highly successful manner as topically applied prodrugs having an enhanced delivery or transport across the topical membrane.

SUMMARY OF THE INVENTION

The above and other objects are realized by the present invention which provides a pharmaceutical composition in unit dosage form adapted for topical administration to a human or non-human animal in need thereof comprising a biologically effective amount of an aminomethyl derivative of a biologically active substance having the formula:

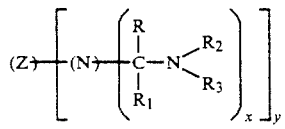
(I)

wherein: $(-Z)-(N)-]_y$ is the N-dehydro residue of a biologically active organic substance having the formula $(-Z)-(N)-(H)_x]_y$ wherein at least one $-(N)-$ is an endocyclic or exocyclic primary or secondary amino, amido or imido nitrogen;

R and $R_1$ may be the same or different and are selected from the group consisting of H, cycloalkl groups having up to 10 carbon atoms, straight or branched chain alkyl, alkenyl and alkynyl groups of 1 to 10 carbon atoms, wherein the chains thereof (1) may be interrupted by at least one N, S or O atom, or (2) may be substituted by at least one group selected from the group consisting of $COR_4$, $COOR_4$ and $CON(R_4)_2$, hydrocarbyl aryl groups, aryl groups substituted by at least one group selected from the groups consisting of $COR_4$, $COOR_4$, $CON(R_4)_2$, $N(R_4)_2$, $OR_4$, halogen, $SR_4$, $NO_2$ and $R_4$, mono- and bi-cyclic saturated or unsaturated heterocyclic rings, each ring consisting of 3 to 7 members selected from the group consisting of carbon, nitrogen, oxygen and sulfur, CN, $COR_4$, $COOR_4$, $CON(R_4)_2$ and $C(halogen)_3$;

$R_2$ and $R_3$ may be the same or different and are selected from the group consisting of H, cycloalkyl groups having up to 10 carbon atoms, straight or branched chain alkyl, alkenyl and alkynyl groups of 1 to 10 carbon atoms wherein the chains thereof (1) may be interrupted by at least one N, S or O atom, and/or (2) may be substituted by at least one group selected from the group consisting of $COR_4$, $COOR_4$ and $CON(R_4)_2$, hydrocarbyl aryl groups, aryl groups substituted by at least one group selected from the group consisting of $COR_4$, $COOR_4$, $CON(R_4)_2$, $N(R_4)_2$, $OR_4$, halogen, $SR_4$, $NO_2$ and $R_4$, mono- and bi-cyclic saturated or unsaturated heterocyclic rings, wherein each ring consists of 3 to 7 members selected from the group consisting of carbon, nitrogen, oxygen and sulfur or together with the nitrogen to which they are bonded may form a mono- or bi-cyclic saturated or unsaturated heterocyclic ring, wherein each ring consists of 3 to 7 members selected from the group consisting of carbon, nitrogen, oxygen and sulfur;

$R_4$ is selected from the group consisting of cycloalkyl groups having up to 10 carbon atoms, straight or branched chain alkyl, alkenyl and alkynyl groups having 1 to 10 carbon atoms, straight or branched chain alkyl, alkenyl and alkynyl groups of 1 to 10 carbon atoms wherein the chains thereof may be interrupted by at least one N, S or O atom, hydrocarbyl aryl groups, and in the case of $—N(R_4)_2$ taken with the other $R_4$ group and N is a mono-or bi-cyclic saturated or unsaturated heterocyclic ring, wherein each ring consists of 3 to 7 members selected from the group consisting of carbon, nitrogen, oxygen and sulfur;

x is an integer from 1 to 2;

y is an integer from 1 to 6; or a non-toxic pharmaceutically acceptable adduct, oxide or other derivative thereof and a pharmaceutically acceptable, topically administrable carrier therefor, the aminomethyl derivative having an enhanced delivery across topical membranes of the animal upon topical application as compared with the underivatized biologically active substance and being capable of exerting the biological activity after delivery across the topical membrane.

The present invention also provides a method of administering a biologically active substance to a human or non-human animal in need thereof comprising topically applying to the animal a biologically effective amount of an aminomethyl derivative of a biologically active substance having the formula set forth in claim 1, or a non-toxic, pharmaceutically acceptable adduct, oxide or other derivative thereof, the aminomethyl derivative having an enhanced delivery across topical membranes of the animal upon topical application as compared with the under vivatized biologically active substance and being capable of exerting the biological activity after delivery across the topical membrane.

The present invention also provides novel aminomethyl derivatives of biologically active compounds, having the formula:

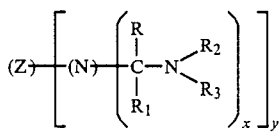

wherein:
- $(-Z)[(N)-]_y$ is the N-dehydro residue of a biologically active organic substance having the formula $(-Z)[(N)(H)_x]_y$, wherein at least one $-(N)-$ is an endocyclic or exocyclic primary or secondary amino nitrogen.
- R and $R_1$ may be the same or different and are selected from the group consisting of H, cycloalkyl groups having up to 10 carbon atoms, straight and branched chain alkyl, alkenyl and alkynyl groups of 1 to 10 carbon atoms wherein the chains thereof (1) may be interrupted by at least one N, S or O atom, or (2) may be substituted by at least one group selected from the group consisting of $COR_4$, $COOR_4$ and $CON(R_4)_2$, hydrocarbyl aryl groups, aryl groups substituted by at least one group selected from the group consisting of $COR_4$, $COOR_4$, $CON(R_4)_2$, $N(R_4)_2$, $OR_4$, halogen, $SR_4$, $NO_2$ and $R_4$, mono- and bi-cyclic saturated or unsaturated heterocyclic rings, each ring consisting of 3 to 7 members selected from the group consisting of carbon, nitrogen, oxygen and sulfur, CN, $COR_4$, $CON(R_4)_2$ and $C(halogen)_3$;
- $R_2$ and $R_3$ may be the same or different and are selected from the group consisting of H, cycloalkyl groups having up to 10 carbon atoms, straight or branched chain alkyl, alkenyl and alkynyl groups having 1 to 10 carbon atoms wherein the chains thereof (1) may be interrupted by at least one N, S or O atom, or (2) may be substituted by at least one group selected from the group consisting of $COR_4$, $COOR_4$ and $CON(R_4)_2$, hydrocarbyl aryl groups, aryl groups substituted by at least one group selected from the group consisting of $COR_4$, $COOR_4$, $CON(R_4)_2$, $N(R_4)_2$, $OR_4$, halogen, $SR_4$, $NO_2$ and $R_4$ and mono- and bi-cyclic saturated or unsaturated heterocyclic rings, wherein each ring consists of 3 to 7 members selected from the group consisting of carbon, nitrogen, oxygen and sulfur or together with the nitrogen to which they are bonded may form a mono- or bi-cyclic saturated or unsaturated heterocyclic ring, wherein each ring consists of 3 to 7 members selected from the group consisting of carbon, nitrogen, oxygen and sulfur;
- $R_4$ is selected from the group consisting of cycloalkyl groups having up to 10 carbon atoms, straight or branched chain alkyl, alkenyl and alkynyl groups of 1 to 10 carbon atoms wherein the chains thereof may be interrupted by at least one N, S or O atom, hydrocarbyl aryl groups, and in the case of $-N(R_4)_2$ taken with the other $R_4$ group and N is a mono- or bi-cyclic saturated or unsaturated heterocyclic group wherein each ring consists of 3 to 7 members selected from the group consisting of carbon, nitrogen, oxygen and sulfur;
- x is an integer from 1 to 2; and
- y is an integer from 1 to 6;

provided that at least one of the $-(N)-$ groups is an amino group; or a non-toxic, pharmaceutically acceptable salt, adduct, oxide or other derivative thereof.

DETAILED DESCRIPTION OF THE INVENTION

The present invention is predicated on the discovery that the N-methylamino derivatives of the above formula I exhibit enhanced water as well as enhanced lipid solubilities thereby rendering them more effective prodrugs for improving topical delivery than prodrugs designed heretofore which merely incorporated lipid solubilizing groups into the parent drug structure.

Any topically applicable, biologically active substance possessing an endocyclic or exocyclic amino, amido or imido NH may be derivatized according to the present invention to provide a prodrug having enhanced delivery or transport across the topical membrane of a human or non-human animal. It will be further understood by those skilled in the art that the term "biologically active organic substance" as used herein also includes drug species which have been converted into prodrugs by derivatization according to other methods. For example, azaribine (O'-acetylated-6-azauridine), a prodrug of 6-azauridine could be converted to an N-aminomethyl prodrug according to the present invention which would be even more effective in delivering the parent drug across topical membranes.

An illustrative but non-exhaustive list of biologically active organic substances susceptible to conversion to aminomethyl derivatives according to the present invention includes: methyl-GAG [HN═C(NH₂)—NH—N═C (CH₃)—CH═N—NH—C(NH₂)═NH, phenytoin, thiabendazol, tolazoline, allopurinol, allantoin, cycloheximide, 6-aminonicotinamide, 2-thiopyridine, 2-aminothia-3, 4-diazole, cyclophosphamide, adamantanamine, 4-aminobutyric acid, propranolol, salicylamide, 5-fluorouracil, theophylline, 6-mercaptopurine, 5-fluorocytosine, 5-iododeoxycytidine, acyclovir, ara-A, 6-thioquanine, tegafur, ribavirin, azacitidine, azaribine, azathioprine, triamterene, razoxane, ribopurine, tisopurine, trimethoprim, hydroxyurea, methotrexate, minoxidil, piroxicam, pyrimethamine, enprofylline, guanazolo, clonidine, sulfamides such as sulfadiazine, sulfisoxasole, benzocaine, lidocaine, procaine, BW 755C, nifedipine, benzyladenosine, mitomycin C, tetracycline, proflavine, penicillins such as penicillin G, cephalosporins such as cefotaxime or cephradine, acetylcysteine, aminoglycosides such as amikacin, aminopterin, 5-substituted uracils, uridines and deoxyuridines such as 5-iododeoxyuridine or uracil mustard, various aza- and deazapurines and pyrimidines as well as their nucleosides and nucleotides, cyclic AMP phosphate ester as well as other nucleotide phosphate esters, desmethyldiazepam, butamisole, barbituric acids such as phenobarbital, salicylamide, carmofur, nitrosoureas such as carmustine, chloramphenicol, clonazepam, cycloserine, cyclosporins, ara-C, dacarbazine, piminodine, and nitrofurantoin.

Particularly preferred biologically active substances are those wherein the $(-Z)(N-)_y$ residues have the formulae:

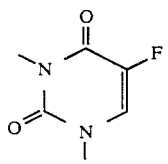
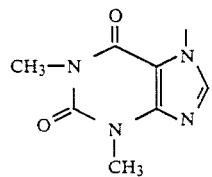
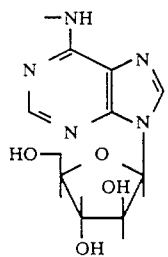
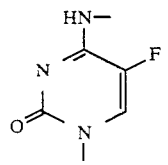
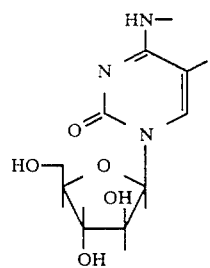
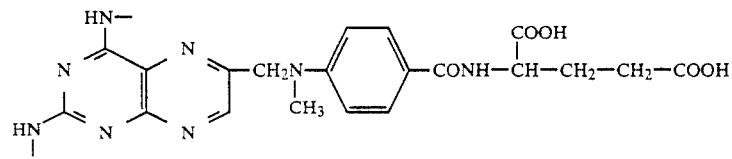
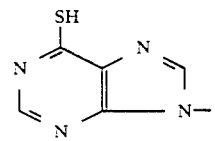
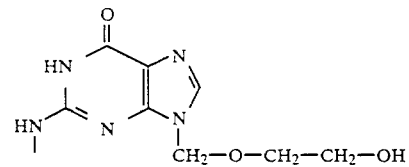

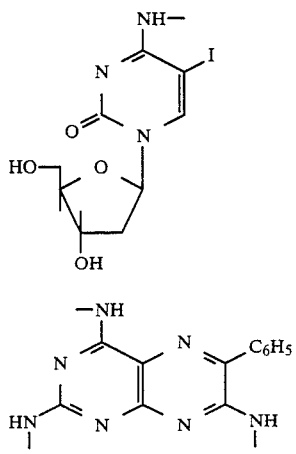

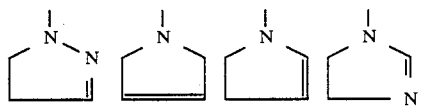

The particular aminomethyl derivative (i.e., the identity of R, $R_1$, $R_2$ and $R_3$ in the above formulas) employed will depend in each case upon a variety of factors, e.g., the effect of the substituents on the water solubility, lipophilicity and other properties of the active drug species, and the stability of the aminomethyl derivatives. For instance, if the parent drug is very polar, $R_2$ and $R_3$ may have to be fairly long chain alkyl groups but, if the parent drug is less polar, shorter chain alkyl groups may suffice to enhance topical delivery. Similarly, the less basic the amino group to which $R_2$ and $R_3$ are attached the more stable the aminomethyl derivative. Thus, if $NR_2R_3$ are combined to give a morpholinyl group (pKa=8.4), the aminomethyl derivative that results will be more stable than if $NR_2R_3$ are combined to give a piperidyl group (pKa=11.2).

As employed herein, the term "alkyl" includes methyl, ethyl, propyl, and butyl and the branched-chain isomers thereof, as well as their straight and branched-chain higher homologues in the instances where "alkyl" can contain more than 4 carbon atoms. The "alkenyl" and "alkynyl" radicals may be straight or branched-chain, for example, vinyl, propenyl, butenyl, ethynyl, propynyl, butynyl, and the like. The cycloalkyl and cycloalkenyl radicals are exemplified by cyclopentyl, cyclohexyl and cyclopentenyl.

"Aryl" includes phenyl, naphthyl, etc. as well as aralkyl, aralkenyl and aralkynyl radicals of the type -alkylene-aryl -alkenylene-aryl and -alkynylene-aryl wherein aryl is as defined above and "alkylene", "alkenylene" and "alkynylene" are as defined above.

Illustrative of residues of saturated monocyclic heterocyclics which are encompassed by the term "heterocyclic" are morpholino, perhydro-1,2,4-oxathiazin-4-yl, 1-pyrrolidinyl, 4-benzyl-1-piperazinyl, 4-methyl-1-piperazinyl, piperidino, hexamethyleneimino, 4-phenylpiperidino, 2-methyl-1-pyrazolidinyl, 3-methyl-1-imidazolidinyl, 4-benzylpiperidino and 4-phenyl-1-piperazinyl. Exemplary of residues of unsaturated one and two ring heterocyclic systems are radicals such as 1-imidazolyl, 1-pyrrolyl, 1-pyrazolyl, 1-indolinyl, 2-isoindolinyl, 1-indolyl, 2-isoindolyl, 1H-indazol-1-yl, and 7-purinyl; and radicals derived from compounds such as pyrazoline, pyrroline and imidazoline wherein there is one secondary nitrogen atom, e.g., radicals of the type and the like. In addition, any of the aforesaid unsaturated one and two ring heterocycles can be optimally substituted with one or more methyl groups.

The term "halogen" includes fluoro, chloro, bromo and iodo groups.

The prodrugs may be prepared according to any of several methods. The parent compound may be allowed to react with:

(1) from one to twenty equivalents of a mixture of a carbonyl compound ($RR_1C=O$) or trimer or polymer thereof and a primary or secondary amine ($H-NR_2R_3$) in an inert solvent such as tetrahydrofuran, dioxane, ether, dichloromethane, dimethylformamide, etc., or in a solvent such as an alcohol or water that may participate in the formation of an intermediate reactant; e.g., $RCH=O+HNR_2R_2$ in ethanol forms $C_2H_5O-CHR-NR_2R_3$ which reacts with the parent compound;

(2) from one to twenty equivalents of RO—CR-$R_2$—$NR_2R_3$ in any of the above mentioned solvent systems;

(3) from one to twenty equivalents of $R_2R_3NCRR_1$—$NR_2R_3$ or RS—$CRR_1$—$NR_2R_3$ in any of the above-mentioned solvent systems;

(4) from one to twenty equivalents of Q—$CR_1$—$NR_2R_3$ where Q is a good leaving group such as chloride, bromide, iodide, tosylate, etc.; or (5) from one to twenty equivalents of a carbonyl compound ($RR_1C=O$) to yield the intermediate Z—N—$CRR_1$—OH which is then reacted with from one to twenty equivalents of a primary or secondary amine ($R_2R_3NH$) in any of the above-mentioned solvent systems.

The reactions can be carried out in the presence or absence of an organic base such as triethylamine at ice bath to reflux temperatures for from 10 minutes to two or three days. The product may then be simply separated by filtration, or the solvent evaporated at reduced pressure and the resultant residue crystallized or triturated then filtered to yield the desired product, or the solvent evaporated to yield the product as an oil or an amorphous solid.

The reactions generally proceed under ambient conditions. In some instances, however, it may be necessary to utilize elevated temperatures in the range of from about 0° to about 100° C. in order to efficiently drive the reaction to completion.

While it is possible for the prodrugs to be administered as the raw substances it is preferable to present them as pharmaceutical formulations. The formulations, both veternary and for human use, of the present invention comprise the prodrug together with one or more acceptable carriers therefor and optionally other therapeutic ingredients. The carrier(s) must be "acceptable" in the sense of being compatible with the other ingredients of the formulation and not deleterious to the recipient thereof. The formulations may conveniently be presented in unit dosage form and may be prepared by any of the methods well known in the art of pharmacy. All methods include the step of bringing into association the prodrug with the carrier which constitutes one or more accessory ingredients. In general, the formulations are prepared by uniformly and intimately bringing into association the prodrug with the carrier(s) and then, if necessary, dividing the product into unit dosages thereof.

It should be understood that excluded from the scope of the present invention are non-sterile mixtures which are mere solutions or suspensions of the known prodrugs in solvents and liquids known in the literature for use in their synthesis and/or isolation by the methods described therein. Included within the scope of the present invention are such solutions and suspensions of the known substances which are pharmaceutically acceptable to the intended recipient thereof and which contain in addition at least one other pharmaceutically acceptable substance.

It will be appreciated that although the prodrugs may form acid addition salts and carboxy acid salts the biological activity—transport or delivery activity—thereof will reside in the basic prodrugs therein. The salts of the novel aminomethyl derivatives may be used in human and in veterinary medicine and presented as pharmaceutical formulations in the manner and in the amounts (calculated as the base) described hereinabove, and it is then preferable that the acid moiety be pharmacologically and pharmaceutically acceptable to the recipient. Examples of such suitable acids include (a) mineral acids: hydrochloric, hydrobromic, phosphoric, metaphosphoric, nitric and sulphuric acids; (b) organic acids; tartaric, acetic, citric, malic, lactic, fumaric, benzoic, glycollic, gluconic, gulonic, succinic and aryl-sulphonic, for example, p-toluenesulphonic acids.

The pharmaceutically and pharmacologically acceptable salts together with those salts which are not so acceptable (for example salts of hydrofluoric and perchloric acids) have utility in isolation and purification of the prodrugs, and of course the unacceptable salts are also valuable in the preparation of the acceptable salts by techniques well known in the art. Those prodrugs containing a plurality of free amino groups may be obtained in the form of mono- or poly-acid addition salts, or as mixed salts of a plurality of acids.

Several prodrugs form complexes with pharmaceutically acceptable metals such as zinc. Such complexes may be prepared by techniques analogous to those well known in the art and may be used in human and veterinary medicine, and presented as pharmaceutical formulations, in the manner and in the amounts (calculated as the prodrugs) described hereinabove.

Suitable non-toxic pharmaceutically acceptable carriers for use with the prodrugs will be apparent to those skilled in the art. See, for example, *Remington's Pharmaceutical Sciences*, 4th Ed. (1970). Obviously, the choice of suitable carriers will depend upon the exact nature of the particular dosage form selected, as well as upon the identity of the active drug species $Z-(N-(H)_x)_y$.

Generally, however, the prodrugs of the present invention for use in topical applications should be restricted to use in non-protic, anhydrous vehicles (e.g., plastibase, petrolatum, isopropyl, myristate, etc.) at concentrations of from about 0.1 to about 20%, by weight. The stability of the prodrug in a particular vehicle will depend not only upon the vehicle employed but also on the pKa of the amine involved. Generally, lower pKa amines will yield more stable prodrugs.

The therapeutic dosage ranges for administration of the prodrugs will generally be the same as, or less than, those characteristically used in this art for administration of the active drug species $Z-(N-(H)_x)_y$. Obviously, such therapeutic dosage ranges will vary with the size of the patient, the condition for which the prodrug is administered, the particular dosage form employed, and the like. The quantity of given dosage form required to deliver the desired dose of active drug $Z-(N-(H)_x)_y$ will, of course, depend upon the concentration of the prodrug in any given pharmaceutical composition dosage thereof.

The invention is illustrated by the following non-limiting examples.

EXAMPLE 1

Preparation and characterization of aminomethyl derivatives of adenosine, cytidine, guanosine and triamterene Table 1 sets forth the structures of the starting materials and products produced by the specific examples described below. Equation 1 depicts the mechanism of the hydrolysis of the products. Note that for the sake of convenience in Example 1 the definitions of R and R' have different meanings than elsewhere and the specific compounds of the example are numbered in a manner that is consistent only within the example.

TABLE 1

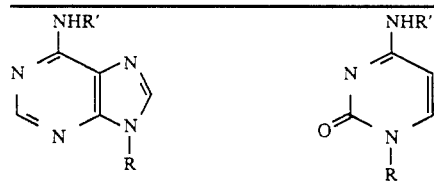

TABLE 1-continued

1a R'=R=H, adenine         2a R'=R=H, cytosine

1b R'=H, R=CH₂N  O      2b R'=H, R=CH₂N  O

2c R'=H, R=CH₂N(C₂H₅)₂
1c R'=H, R=CH₂N 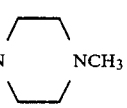 NCH₃

1d R'=R=CH₂N  O        2d R'=R=CH₂N  O

1e R'=R=CH₂N ⌬          2e R'=R=CH₂N ⌬

1f R'=R=CH₂N(C₂H₅)₂        2f R'=R=CH₂N(C₂H₅)₂

1g adenosine               2g cytidine

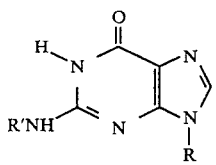       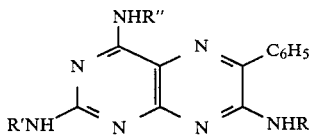

3a R'=R=H, guanine         4a R''=R'=R=H, triamterene

3b R'=R=CH₂N(CH₃)₂

4b mono-CH₂N 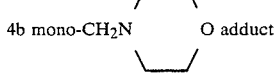 O adduct 3c guanosine 4c bis-CH₂N ⌬ O adduct, bis-CH₂OH adduct Equation 1

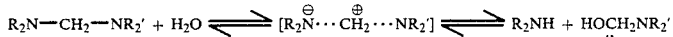

R₂N = purine or pyrimidine

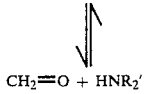

Formally, the reaction of an amine with formaldehyde and another amine is an aminomethylation, i.e., an alkylation, and as such it belongs to the same class of reactions as the Mannich and Einhorn reactions, except that in the latter cases the acceptor of the aminomethyl group is acidic. In the starting materials in methods for the preparation of the prodrugs, e.g., adenine and cytosine of the invention, one of the acceptors, the endocyclic amino group, is acidic (acid pKas 9.3 to 12.6), but the other acceptor, the exocyclic amino groups, e.g., on the purines or pyrimidine, exhibits a low, basic pKa (−3.0 to 1.7). Since the Mannich and Einhorn adducts hydrolyze at rates that are dependent on the acidity of the acceptor and the basicity of the amine, their formation in a partially aqueous environment should depend on the same variables. Therefore, it was anticipated that the structure of the isolated products of the invention would depend on the basicity of the secondary amine used in the reaction since there were several possible akylation sites which exhibit quite different acidities and basicities.

This was indeed found to be the case with adenine. For amines exhibiting low basicity (morpholine, pKa 8.36, and N-methylpiperazine, on the basis of piperazine pKas 5.68, 0.82), if only one equivalent of secondary amine - formaldehyde was used, a mono-adduct was isolated. If one equivalent of formaldehyde and the more basic amines were used (piperidine, pKa 11.22, and diethylamine, pKa 10.98), no mono-adducts were isolated from the reactions; only mixtures of adenine and bisadducts were observed. In the case of the less basic amines the use of three to four equivalents of amine-formaldehyde was necessary to drive the reaction completely to bis-adducts, while if the more basic amines were used, only two equivalents of the amine-formaldehyde mixture were needed. In the latter case, if excess equivalents (three to four) of amine-formaldehyde were used, additional N—CH$_2$—N or N—CH$_2$—O type absorptions, whose origins were not determined, were observed in the NMR spectra of the reaction mixtures. The small K values observed by McGhee et al, Biochemistry, 10, 254 (1971) for the addition of a second hydroxymethyl group to the exocyclic amine in adenosine and the relatively small excess of amine-formaldehyde used in the present experiments suggested that the extraneous absorptions observed were not due to N(CH$_2$NR$_2$)$_2$.

The NMR spectra of the bis-adducts of adenine showed two different N—CH$_2$—N absorptions. The upfield absorptions were doublets which collapsed to singlets on D$_2$O exchange. At the same time triplets in each spectrum that integrated for one proton disappeared. Thus, one of the N—CH$_2$—N absorptions was coupled to an NH absorption, and the only possibility was that it was due to the product of the alkylation of the exocyclic amino group in adenine. The downfield absorption could then be due to alkylation at a number of different sites: 1, 3, 7, or 9. However, the UV spectrum of 1d was more similar to the N$^6$,9-dibenzyladenine isomer and to adenine itself than to the other dibenzyl isomers (a bathochromic shift of UV max in going from neutral to basic solution and from neutral to acidic solution). In addition, the positions of the carbon absorptions in the $^{13}$C NMR spectrum of the bis-adduct 1d were identical with the positions of the ring carbon absorptions in the $^{13}$C NMR spectra of the 9-substituted adenines reported by Chenon et al, J. Am. Chem. Soc., 97, 4627 (1975). This clearly excluded the 7-position as an alternate alkylation site to account for the substitution pattern in 1d. Thus, the adenine bisadducts have been assigned the N$^6$,9-substituted structure on the basis of the structure of 1d.

The structure of the two mono-adducts that were isolated from the reaction of one equivalent of lower basicity amine-formaldehyde with adenine was derived from the similarity of the NCH$_2$H absorptions in their NMR spectra to that of the bis-adducts. In each case the N—CH$_2$—N absorption was at the same position as the downfield N—CH$_2$—N absorption in the bis-adduct. In addition, the UV spectra of the mono-adducts were essentially identical with adenine which has an 9-H structure. Thus, the monoadducts have been assigned a 9-alkylated structure.

There was no change in the type of product isolated from the reaction of amine-formaldehyde with cytosine that resulted from a change in either the basicity of the amine used or the number of equivalents used; no 2b or 2c were observed under any conditions from the reaction of cytosine with formaldehyde, and morpholine or diethylamine. If only one equivalent was used, mixtures of bis-adduct and unreacted cytosine were isolated. Usually, the use of four equivalents of aminomethylating agent was necessary to drive the reaction completely to bis-adduct.

The NMR spectra of the bis-adducts of cytosine were very similar to that of the bis-adducts of adenine. The upfield absorption due to N—CH$_2$—N were again doublets in most cases, which collapsed to singlets on D$_2$O exchange in all cases and were coupled to an exchangeable absorption which integrated for one proton. Thus, the upfield N—CH$_2$—N absorptions were due to alkylation on the exocyclic amino group. The remaining N—CH$_2$—N absorptions in the spectra of the bis-adducts could be due to alkylation on either the 1- or the 3-position. However, the UV spectra of the bis-adducts were similar to the UV spectra of 1-, N$^4$, N$^4$-, or .1, N$^4$-substitution patterns or cytosine itself; exhibition of bathochromic shifts of the UV max on going from neutral to acid or basic solution whereas 3-substituted cytosines without a 1-substituent exhibited a large hypsochromic shift of the UV max on going from neutral to acid solution. In addition the $^{13}$D NMR spectrum of the bis-adduct 2d was essentially identical to that reported for cytidine. Jones et al, Proc. Nat. Acad. Sci., 65, 27 (1970). Thus, the cytosine bis-adducts have been assigned N$^4$, 1-substituted structures.

In the case of the reaction of guanine with formaldehyde-amine the products from the reactions were solids which exhibited high melting points (270° C.) and which were insoluble in solvents used for NMR spectroscopy. The only solvent in which an $^1$H NMR spectrum could be determined was CF$_3$CO$_2$H (for 3b) but that spectrum suggested that the sample had decomposed. The elemental analyses of 3b suggested that it was a bis-adduct. Analogy to previous work with formaldehyde adducts of guanosine and the thiophenol-formaldehyde adducts of guanosine, suggested that the exocyclic amine was alkylated, and analogy to the remainder of the present work suggested that the 9-position was alkylated. Thus, the bis-alkylated guanine derivative 3b has been assigned the N$^2$, 9-substituted structure.

A pteridine was also included in the analysis because of the importance of pteridine structures in biology. Triamterene was chosen because of its commercial availability and because of interest in using aldehyde adducts of triamterene to increase its water and lipid solubilities. There were two types of reactions between formaldehyde-amine and triamterene. The first reaction involved the formation of a mon-adduct which in the case of the morpholine-formaldehyde adduct 4b was isolated as its THF solvate. The $^1$H NMR spectrum of the mono-adduct 4b showed one set of NH—CH$_2$—N absorptions in which the doublets due to the CH$_2$ absorption collapsed to a singlet when the NH absorption was exchanged with D$_2$O. Thus, the mono-adduct appears to be derived from alkylation on one of the three exocyclic amines.

When excess equivalents of alkylating agents were used, the portion of monoalkylated product decreased and a second product 4c was isolated in increasing amounts. The second product contained the elements of two amino-methylations and two hydroxymethylations on the basis of $^1$H NMR spectroscopy and elemental analyses. Similar results were obtained when pyrrolidine was used instead of morpholine in the reactions; a mono-adduct was obtained in good yield when one equivalent of amine-formaldehyde was used but a second (multi-alkylated) product was obtained in progressively higher yield as more equivalents were used.

The formation of the aminomethyl adducts with cytosine and adenine was reversible in dilute aqueous solution. The rates of hydrolysis for the mono-adducts of adenine were not determined because the rates were determined by UV and the UV spectra of the mono-adducts were identical with adenine. However, the rates of hydrolysis of the bis-adducts could be determined by UV spectroscopy because their UV spectra were different from adenine and cytosine. It was not possible to determine by UV whether both aminomethyl groups came off or only that on the exocyclic amino group in the adenine adduct because of the identity of the UV spectra of adenine with the endocyclic amine alkylated adduct. In the case of the bis-adducts, the basicity of the amines influenced the rates of hydrolysis, as expected, because of their similarity to the Mannich base chemistry. The morpholine adduct 1d was much slower ($t\frac{1}{2}$=about 30 min.) than the piperidine adduct 1e ($t\frac{1}{2}$=about 5 min.). The cytosine bis-adduct 2d was much slower yet; it exhibited a $t\frac{1}{2}$ of about 3 hr. The order of these rates of hydrolyses for the aminomethylated products were comparable to the rates of hydrolyses observed by Bridson et al (J. Chem. Soc., Chem. Comm. 1980, 208), for the ethoxymethyl derivatives of the protected nucleosides.

Although UV spectroscopy was not capable of determining whether both aminomethyl groups were being lost in the hydrolyses, $^1$H NMR spectroscopy definitely showed that both N—$CH_2$—N absorptions were being lost as new equilibria between N-aminomethylated product and parent purine or pyrimidine were established with each addition of $D_2O$ (see Equation 1) until all of the N—$CH_2$—N absorptions were gone. However, it was also clear on the basis of the integration of the absorptions due to the two types of N—$CH_2$—N that the aminomethylation of the exocyclic amino group was more easily reversible as the absorption due to NH—$CH_2$—N decreased in intensity faster. No N—$CH_2$—OH type absorptions were observed by NMR spectroscopy during the hydrolyses.

The aminomethylations of purines, pyrimidines and pteridines takes place easily at room temperature and the products of the reactions were crystalline, readily isolated, and easily characterized by UV, NMR and elemental analyses. The aminomethylation reaction is also easily reversible in dilute aqueous solution. Thus, aminomethylation exhibits the same characteristics as the hydroxymethylation reactions but offer the distinct advantage that the products may be isolated and characterized in the case of the purine and pyrimidine bases themselves.

THE REACTION OF ADENINE WITH ONE EQUIVALENT OF SECONDARY AMINE AND FORMALDEHYDE

To a THF (4 ml) solution of 0.29 g (0.0033 mole) of morpholine and 0.27 g (0.0033 mole) of 37% $H_2C=O$ in water was added 0.45 g (0.0033 mole) of adenine. The suspension was stirred at room temperature for 4 days, then it was filtered to give 0.50 g [foamed at 99°–104°, >240° (d)] of the 9-(4'-morpholinyl)methyladenine (1b): 67% yield: IR (KBr) 3520, 3400, 3270 and 3080 $cm^{-1}$ (M) (N—H and OH), and 1675 and 1605 $cm^{-1}$ (S); $^1$NMR (DMSO-$d_6$) $\delta$8.07 (s,1, $C_2$—H), 7.97 (s,1, $C_8$—H), 7.3–6.8 (m, 2, N—H, exchangeable with $D_2O$), 4.97 (s, 2, N—$CH_2$—N), 3.8–3.3 (m, 4, C—$CH_2$—O), 3.33 (s, 2, $H_2O$) and 2.7–2.35 (m, 4, C—$CH_2$—N); UV ($CH_3OH$) max 261 nm ($\epsilon=1.29\times 10^4$ 1/mole), OH$^\ominus$ 271 nm ($\epsilon=1.19\times 10^4$ 1/mole) and H$^\oplus$ 264 nm ($\epsilon=1.27\times 10^4$ 1/mole).

Anal. Calcd for $C_{10}H_{14}N_6O \cdot H_2O$: C, 47.61, H, 6.39; N, 33.32. Found: C, 47.60; H, 6.42; N, 33.34.

9-(4'-Methyl-1'-piperazinyl)methyladenine (1c) was prepared in a similar manner:

68% yield, foam 132°–146°, decomposed 226°–248°; IR(KBr) 3450 and 3100 $cm^{-1}$ (M) (N—H and OH), 1640 and 1660 $cm^{-1}$ (S); $^1$H NMR (DMSO-$d_6$) $\delta$8.13 (s, 1, $C_2$—H), 8.08 (s, 1, $C_8$—H), 7.4–6.9 (m, 2, N—H), 5.0 (s, 2, N—$CH_2$—N), 3.6–3.0 (m, 2, OH), 2.7–2.0 (m, 8, $CH_2$—N) and 2.08 (s, 3, $CH_3N$). Although the spectral dates were consistent with a mono-hydrate of the mono-adduct, correct elemental analyses could not be obtained for the product.

THE REACTION OF ADENINE WITH TWO OR MORE EQUIVALENTS OF SECONDARY AMINES AND FORMALDEHYDE

Generally 3 to 4 equivalents of a 1:1 mixture of the secondary amine and 37% aqueous formaldehyde in tetrahydrofuran (10 ml for 0.01 mole scale) were allowed to react with adenine at room temperature overnight in order to drive the reaction to completion. The solutions that resulted were concentrated and those concentrates were triturated with ether for 2–5 hr, then filtered. The residues were usually analytically pure. However, in those cases where the secondary amine was diethylamine or other amines where there were more degrees of vibrational freedom available to the alkyl substituents, the concentrates were oils and the excess alkylating agent could not be easily separated from the product. Then, only 2 equivalents of secondary amine and formaldehyde were used. Any unreacted adenine was filtered from the reaction mixture at the trituration stage and the oils were characterized as such. Thus, the following bis-adducts were obtained:

Bis-$N^6$,9-(4'-morpholinyl)methyladenine (1d): mp 142°–144°, 91% yield; IR (KBr) 1630 $cm^{-1}$ (S), and 3260 and 3200 $cm^{-1}$ (W) (N—H); $^1$H NMR (CDCl$_3$) $\delta$8.33 (s, 1, $C_2$—H), 7.8 (s, 1, $C_8$—H), 6.53 (t, 1, J=6 Hz, N—H, $D_2O$ exchangeable), 5.0 (s, 2, N—$CH_2$—N), 4.55 (d, 2, J=6 Hz, NH—$CH_2$N, collapses to a singlet on $D_2O$ exchange), 3.8–3.55 (m, 8, C—$CH_2$—O) and 2.8–2.45 (m, 8, $NCH_2$—C); $^{13}$C NMR (DMSO-$d_6$) $\delta$152.47 ($C_2$), 150.30 ($C_4$), 118.46 ($C_5$), 155.20 ($C_6$) and 141.56 ($C_8$); UV ($CH_3OH$) max 269 nm ($\epsilon=1.59\times 10^4$ 1/mole), OH$^\ominus$ 274 nm ($\epsilon=1.51\times 10^4$ 1/mole) and H$^\oplus$ 270 nm ($\epsilon=1.30\times 10^4$ 1/mole.)

Anal. Calcd for $C_{15}H_{23}N_7O_2$: C, 54.04; H, 6.95; N, 29.41.

Found: C, 53.97; H, 6.99; N, 29.35.

Bis-$N^6$,9-(1'-piperidinyl)methyladenine (1e); mp 139°–141°, 68% yield; IR (KBr) 1620 $cm^{-1}$ (S), and 3240 and 3160 $cm^{-1}$ (W) (N—H); $^1$H NMR (CDCl$_3$) $\delta$8.33 (s, 1, $C_2$—H), 7.77 (s, 1, $C_8$—H), 6.3–6.0 (m, 1, N—H, $D_2O$ exchangeable), 5.0 (s, 2, N—$CH_2$N) 4.55 (d, 2, J=6 Hz, $NHCH_2$—N, collapses to a singlet on $D_2O$ exchange), 2.75–2.4 (m, 8, C—$CH_2$N) and 1.85–1.0 (m, 12, $CH_2$—$CH_2$—$CH_2$); UV ($CH_3OH$) max 267 nm ($\epsilon=1.65\times 10^4$ 1/mole), OH$^\ominus$ 274 nm ($\epsilon=1.54\times 10^4$ 1/mole) and H$^\oplus$ 270 nm ($\epsilon=1.44\times 10^4$ 1/mole).

Anal. Calcd for $C_{17}H_{27}N_7$: C, 61.98; H, 8.26; N, 29.76.

Found: C, 61.89; H, 8.30; N, 29.72.

Bis-$N^6$,9-(diethylamino)methyladenine (1f): an oil, 67% yield; $^1$H NMR (CDCl$_3$) $\delta$8.30 (s, 1, $C_2$—H), 7.77 (s, 1, $C_8$—H), 6.2–5.8 (m, 1, N—H, $D_2O$ exchangeable), 5.07 (s, 2, N—$CH_2$—N), 4.70 (d, 2, J=6 $H_z$, NH—$CH_2$—N, collapses to a singlet on $D_2O$ exchange), 2.8 (q, 4, J=7 Hz, $CH_2$N), 2.83 (q, 4, J=7 Hz, $CH_2$N) and 1.13 (t, 12, J=7 Hz, $CH_3$—$CH_2$—N).

Anal. Calcd. for $C_{15}H_{27}N_7 \cdot 0.5 H_2O$: C, 57.29; H, 8.98; N, 31.19.

Found: C, 57.62; H, 8.70; N, 31.32.

THE REACTION OF CYTOSINE WITH TWO OR MORE EQUIVALENTS OF SECONDARY AMINES AND FORMALDEHYDE

Generally 3 to 4 equivalents of a 1:1 mixture of secondary amine and 37% aqueous formaldehyde in tetrahydrofuran (10 ml for 0.01 mole scale) were allowed to react at room temperature with cytosine overnight. The suspensions were kept well stirred and (except for the cases where the secondary amine was diethylamine or other amine with more degrees of vibrational freedom available to the alkyl substituents) the suspensions were filtered. These residues were analytically pure products. With diethylamine and similar secondary amines, clear solutions were obtained after reaction overnight. The solutions were concentrated and the residues were triturated with ether or hexane to give the desired compound as suspended white solids which were isolated by filtration. Thus, the following bis-adducts were obtained:

Bis-$N^4$,1-(4'-morpholinyl)methylcytosine (2d): mp 192°-193°, 83% yield; IR (KBr) 3260 cm$^{-1}$ (M) (N—H), and 1655 and 1630 cm$^{-1}$ (S); $^1$H NMR (DMSO-d$_6$) δ7.75 (t, 1, J=5 Hz, NH, D$_2$O exchangeable), 7.41 (d, 1, J=8 Hz, CH=C), 5.65 (d, 1, J=8 Hz, CH=C), 4.43 (s, 2, N—CH$_2$—N), 4.08 (d, 2, J=6 Hz, NH—CH$_2$N, collapses to a singlet on D$_2$O exchange), 3.7–3.4 (m, 8, C—CH$_2$—O) and 2.65–2.3 (m, 8, C—CH$_2$—N); $^{13}$C NMR (DMSO-d$_6$) δ156.26 (C$_2$), 164.54 (C$_4$), 93.48 (C$_5$) and 145.45 (C$_6$); UV (CH$_3$OH) max 270 nm (ε=7.77×10$^3$ 1/mole), OH$^\ominus$ 276 nm (ε=7.25 ×10$^3$ 1/mole) and H$^\oplus$ 282 nm (ε=10.8×10$^3$ 1/mole).

Anal. Calcd. for $C_{14}H_{23}N_5O_3$: C, 54.35; H, 7.49; N, 22.64.

Found: C, 54.42; H, 7.50; N, 26.63.

Bis-$N^4$, 1-(1'-piperidinyl)methylcytosine (2e): mp 195°-196°, 94% yield; IR (KBr) 3260 cm$^{-1}$ (M) (N—H), and 1650 and 1630 cm$^{-1}$ (S); $^1$H NMR (CDCL$_3$) δ7.37 (d, 1, J=8 Hz, CH=C), 5.70 (d, 1, J=8 Hz, CH=C), 6.4–5.4 (broad m, 1, N—H), 4.47 (s, 2, N—CH$_2$—N), 4.15 (m, 2, NH—CH$_2$N), 2.65–2.2 (m, 8, C—CH$_2$—N) and 1.8–1.2 (m, 12, C—CH$_2$—C); UV (CH$_3$OH) max 272 nm (ε=6.34×10$^3$ 1/mole), OH$^\ominus$ 280 nm (ε=6.61×10$^3$ 1/mole) and H$^\oplus$ 282 nm (ε=1.13×10$^4$ 1/mole).

Anal. Calcd. for $C_{16}H_{27}N_5O$: C, 62.92; H, 8.91; N, 22.93.

Found: C, 63.08; H, 8.95; N, 22.87.

Bis-$N^4$, 1-(diethylamino)methylcytosine (2f): mp 134°-136°, 75% yield; IR (KBr) 3230 cm$^{-1}$ (M) (N—H), 1640 and 1620 cm$^{-1}$ (S); $^1$H NMR (CDCL$_3$) δ7.47 (d, J=8 Hz, 1, CH=C) 5.73 (d, J=8Hz, 1, CH=C), 6.2–5.6 (m, 1, N—H), 4.53 (s, 2, N—CH$_2$—N), 4.6–4.0 (m, 2, NH—CH$_2$N) 2.7 (q, 4, J=7 Hz, CH$_2$—N), 2.50 (q, 4, J=7 Hz, N—CH$_2$) and 1.03 (t, J=7 Hz, 12, CH$_3$CH$_2$N); UV (CH$_3$O—H) max 270 nm (ε=7.10×10$^3$ 1/mole), OH$^\ominus$ 279 nm (ε=7.18×10$^3$ 1/mole) and H$^\oplus$ 281 nm (ε=1.31×10$^4$ 1/mole).

Anal. Calcd. for $C_{14}H_{27}N_5O$: C, 59.75; H, 9.67; N, 24.89.

Found: C, 59.55; H, 9.59; N, 24.84.

THE REACTION GUANINE WITH AN EXCESS OF FORMALDEHYDE AND DIMETHYLAMINE

Guanine (0.38 g, 0.0025 mole) was suspended in 2.2 g (0.02 mole) of 40% dimethylamine in water. Then, 1.62 g (0.02 mole) of 37% CH$_2$=O) was added and the suspension was stirred at room temperature for 1 day. The suspension was diluted with THF. The THF-water suspension was stirred for 2 hr, then filtered, and the residue was dried to give 0.62 g (mp>260°) of white solid which was the desired bis-adduct, 3b; 94% yield; IR (KBr) 3250 cm$^{-1}$ (S) 3600-2200 cm$^{-1}$ (M) (N—H), 1695 cm$^{-1}$ (shoulder), 1685 cm$^{-1}$ (S) (C=O).

Anal. Calcd. for $C_{11}H_{19}N_7O$: C, 49.79; H, 7.22; N, 36.96.

Found: C, 49.58; H, 7.25; N, 36.91.

THE REACTION OF TRIAMTENENE WITH MORPHOLINE AND FORMALDEHYDE

To a THF (6 ml) solution containing 0.22 g (0.0025 mole) of morpholine and 0.21 g (0.0025 mole) of 37% formaldehyde in water was added 0.63 g (0.0025 mole) of triamterene. The suspension was stirred at room temperature overnight then it was filtered to give 0.82 g (mp 222°-224°, 77% yield) of the tetrahydrofuran solvate of a mono-(4'-morpholinyl(methyl adduct with triamterene, (4b): IR (KBr) 3500-2600 cm$^{-1}$ (M) (N—H) and 1630 cm$^{-1}$ (S); $^1$H NMR (DMSO-d$_6$) δ7.85-7.30 (m, 5, aromatic-H), 7.30–6.20 (2 broad s centered at 7.05 and 6.60, 5, NH, exchangeable with D$_2$O), 4.15 (d, 2, J=5 Hz, NH—CH$_2$N, collapses to a singlet on D$_2$O treatment), 3.75–3.2 (m, 8, C—CH$_2$—O), 2.7–2.3 (m, 4, C—CH$_2$N) and 1.9–1.6 (m, 4, C—CH$_2$—C).

Anal. Calcd. for $C_{21}H_{28}N_8O_2$: C, 59.41; H, 6.65; N, 26.44.

Found: C, 59.28; H, 6.72; N, 26.80.

When 4 equivalents of the THF solution of morpholine and formaldehyde on the same mole scale as above was used and the suspension as above was filtered a 45% yield of the mono-adduct was obtained. In that case the filtrate was concentrated and the residue was triturated with 40 ml of ether overnight to give 0.32 g (mp 118°-122° with foaming, 25% yield) of a bis-(4'-morpholinyl)methyl adduct with triamterene which also contained the additional elements of two hydroxymethyl adducts per molecule of triamterene (4c): IR (KBr) 3400-3300 cm$^{-1}$ (M) (N—H and OH); $^1$H NMR (CDCL$_3$) δ7.65-7.35 (m, 5, aromatic-H), 7.2–6.8 (m, 1, N—H), 6.4–6.0 (m, 1, N—H), 5.3–4.8 (m, 4, N—CH$_2$O), 4.6–4.1 (m, 4, N—CH$_2$—N), 3.8–3.4 (m, 8, C—CH$_2$—O) and 2.8–2.35 (m, 8, C—CH$_2$—N).

Anal. Calcd. for $C_{24}H_{33}N_9O_4$: C, 56.34; H, 6.50; N, 24.64.

Found: C, 56.35; H, 6.68; N, 24.51.

STABILITY AND RATES OF HYDROLYSIS OF ADDUCTS

The methanol UV spectra of the adducts of cytosine and adenine were stable for up to 2 hr. The water UV spectrum of the mono-adduct of adenine 1b was essentially identical with adenine itself under the same conditions. The water (pH 7.6) UV spectra of the bisadducts of cytosine and adenine exhibited UV max shifted to longer wavelengths (UV max of adducts in water same as UV max of adducts in methanol) which were more intense than the parent pyrimidine or purine. The rates of hydrolysis of three of the adducts (1d, 1e and 2d) were followed by UV at about 1×10$^{-4}$ mole/l by following the decrease in intensity of their respective UV max with time. Spectra were monitored until stable spectra were produced which in all cases were essentially identical with the parent purine or pyrimidine. Plots of At-At$\infty$ versus time were used to determine t ½. The hydrolyses of the adducts were also followed by ¹H NMR spectroscopy. Solutions (DMSO-d$_6$) of the adducts at about 30 mg/ml, were diluted with D$_2$O in a dropwise fashion until a 1:1 ratio of the two solvents was reached. Integrations (5 times) of the spectra were taken after each addition of D$_2$O. Comparison of the average of the integrations of the N—CH$_2$—N absorptions and the integrations of the C$_2$—H, C$_8$—H, C$_5$—H or C$_6$—H absorptions was used to quantitate the amount of decomposition.

EXAMPLE 2

Preparation of 1,3-di(4-morpholinyl) methyl-5-fluorouracil

A prodrug of 5-FU was prepared by allowing 5 FU to react with three equivalents of 37% formaldehyde in water and three equivalents of morpholine at room temperature for two hours. The solution that resulted was diluted with acetone and the acetone solution was evaporated at water aspirator pressure at 40° C. The residue that was obtained was redissolved in acetone and the solution was again concentrated. The residue from evaporation of the acetone solution was then triturated with ether and that suspension was filtered to give a 41% yield of the 1,3-di(4-morpholinyl)methyl-5-fluorouracil, mp 137°-139°, which exhibited an NMR spectrum consistent with di-N-alkylation and which exhibited one spot upon analysis by TLC.

EXAMPLE 3

Preparation of 7-(1-pyrrolidinyl) methyltheophylline

Equivalent amounts of theophylline and triethylamine were allowed to equilibrate with 2 equivalents of 37% aqueous H$_2$C=O for a few minutes until a solution was obtained. Then, 2 equivalents of pyrrolidine was added and the mixture was diluted with tetrahydrofuran and allowed to stir at room temperature overnight. The solution was then concentrated in vacuo at <40°. The residue was triturated with ether and the suspension filtered. The residue from the suspension was dried to give the desired 7-(1-pyrrolidinyl)methyltheophylline in 72% yield; mp 105°-108°, lit mp 108° (J. Org. Chem. 24, 562 (1959); NMR, UV and TLC consistent with the desired product.

EXAMPLE 4

Preparation of 1,N$^4$-di(4-morpholinyl)methyl cytosine

The desired product was prepared by adding three equivalents of morpholine to three equivalents of 37% H$_2$C=O in water and diluting the solution with THF (about 10:1). Then cytosine was added and the suspension was stirred for two days at room temperature. The suspension was filtered and the residue dried to give the desired 1,N$^4$-di(4-morpholinyl)methylcytosine in 83% yield as a white solid mp 192°-193°.

EXAMPLE 5

Preparation of 9-(N-piperidyl)methyl-6-mercaptopurine

Method A: To a solution consisting of 0.44 g (0.003 mole) of 1-ethoxymethyl-piperidine in 5 ml of THF was added 0.25 g (0.0015 mole) of 6-MP.H$_2$O. The resulting suspension was stirred at room temperature overnight. The suspension was filtered to give 0.35 g (94.6% yield, mp 226°-228° C. (d) of the product as an off-white solid: ¹H NMR (DMSO-d$_6$) δ 8.17 (broad m, 2, 8-H, 2-H), 5.00 (broad s, 2, N—CH$_2$—N), 2.47 (m, 4, N—CH$_2$—CH$_2$), 1.37 (m, 6, N—CH$_2$—CH$_2$—CH$_2$); IR (KBr) 3450 cm$^{-1}$ (VW) (N—H), 1587 cm$^{-1}$ (S) (C=S); UV (MeOH) λ max 329 nm ($\epsilon$=2.48×10$^3$), λ max (HCl) 331 nm ($\epsilon$=2.25×10$^3$), λ max (NaOH) 316 nm ($\epsilon$=2.59×10$^3$).

Anal: Calcd. for C$_{11}$H$_{13}$N$_5$S: C, 52.99; H, 6.06; N, 28.09; S, 12.86.

Found: C, 53.02; H, 6.08

Method B: To 0.85 g (0.01 mole) of piperidine was added 0.43 g (0.0025 mole) of 6-MP.H$_2$O. The suspension that resulted was sonicated while 1.5 ml of H$_2$O was added to give a solution. To the solution was added 0.81 g (0.01 mole) of 37% aqueous formaldehyde. An exothermic reaction ensued resulting in the precipitation of a white solid. The resulting thick suspension was thinned by adding 15 ml of THF and this suspension was stirred at room temperature overnight. The suspension was filtered to give 0.62 g (99.5% yield, mp 222°-224° C. (d)) of a white solid: ¹H NMR (DMSO-d$_6$) δ8.2 (broad m, 2, 8-H, 2-H), 5.00 (broad s, 2, N—CH$_2$—N), 2.47 (m, 4, N—CH$_2$ CH$_2$), 1.37 (m, 6, N—CH$_2$—CH$_2$—CH$_2$); IR (KBr) 3450 cm$^{-1}$ (VW) (N—H), 1587 cm$^{-1}$ (S) (C=S).

EXAMPLE 6

Preparation of 9-(N-diethylamino)methyl-6-mercaptopurine

To 0.37 g (0.0022 mole) of 6-MP.H$_2$O was added 0.77 g (0.0105 mole) of diethylamine. The suspension was sonicated while 1 ml of H$_2$O was added to give a clear, yellow solution. To this solution was added 0.81 g (0.01 mole) of 37% aqueous formaldehyde. The yellow solution was stirred at room temperature overnight. The yellow solution was concentrated to yield a yellow oil. The oil was triturated with ether to give 0.38 g (73.1% yield, mp 169°-173° C. (d)) of the product as an off-white solid: ¹H NMR (DMSO-d$_6$) δ8.17-9.17 (very broad m, 1, N—H), 8.27 (s, 2, 8—H, 2—H), 5.17 (broad, s. 2, N—CH$_2$—N), 2.57 (q, 4, N—CH$_2$—CH$_3$, J=6.5 Hz), 1.00 (t, 6, N—CH$_2$—CH$_3$, J=6.5 Hz); IR (KBr) 3385 cm$^{-1}$ (VW) (N—H), 2970 cm$^{-1}$ (W) (C—H), 1590 cm$^{-1}$ (S) (C=S); UV (MeOH) λmax 330 nm ($\epsilon$=1.87×10$^4$), λmax (HCl) 332 nm ($\epsilon$=1.76×10$^4$), λmax (NaOH) 316 nm ($\epsilon$=2.09×10$^4$).

Anal: Calcd. for C$_{10}$H$_{15}$N$_5$S: C, 50.61; H, 6.37; N, 29.51; S, 13.51.

Found: C, 50.42; H, 6.42.

EXAMPLE 7

Preparation of 9-(N-pyrrolidyl)methyl-6-mercaptopurine

To 0.43 g (0.0025 mole) of 6-MP.H$_2$O was added 0.71 g (0.01 mole) of pyrrolidine. Water (1 ml) was added to the suspension and it was sonicated to give a clear yellow solution. To this solution was added 0.81 g (0.01 mole) of 37% aqueous formaldehyde. An exothermic reaction ensued with subsequent precipitation of a solid. The suspension was stirred at room temperature for 30 min. before adding 5 ml of the THF. The resulting suspension was stirred at room temperature for 1 day. The suspension was filtered to give 0.49 g (84.5% yield, mp 194°-196° C. (d)) of the product as an off-white solid: ¹H NMR (DMSO-d$_6$) δ8.22 (s, 1, 8—H or 2—H), 8.18 (s, 1, 8—H or 2—H), 5-5.5 (broad s, 2, N—CH$_2$—N), 2.5 (m, 4, N—CH$_2$—CH$_2$), 1.62 (m, 4, N—CH$_2$—CH$_2$); IR (KBr) 2960 and 2800 cm$^{-1}$ (M) (C—H str), 1595 cm$^{-1}$ (S) (C=S); UV (MeOH) λmax 331 nm ($\epsilon$=1.95×10$^4$), λmax 223 nm ($\epsilon$=8.96×10$^3$), λmax (HCl) 332 nm ($\epsilon = 1.77 \times 10^4$), λmax 228 nm ($\epsilon = 8.29 \times 10^3$), λmax (NaOH) 317 nm ($\epsilon = 2.02 \times 10^4$), λmax 236 nm ($\epsilon = 1.30 \times 10^4$).

Anal. Calcd. for $C_{10}H_{13}N_5S$: C, 51.04; H, 5.57; N, 29.76; S, 13.62.

Found: C, 51.20; H, 5.62.

EXAMPLE 8

The following examples demonstrate the enhanced delivery of the prodrugs of the invention across topical membranes.

Theophylline and 5-fluorouracil (5-FU) were chosen for derivatization and study because investigations of the effect of their N-acyloxyalkyl derivatives on delivery of the parent compounds relative to the parent compounds was already available in the literature (Sloan et al, supra; Mollgaard et al, supra). Thus, a ready comparison could be made between the effectiveness of the respective derivatives in delivering theophylline and 5-FU, and hence other heterocyclic polar drugs.

In addition, in the case of 5-FU, there were some differences in the literature concerning how well 5-FU was delivered from propylene glycol (Mollgaard et al, supra (1982) versus Cohen et al, J. Invest. Dermatol. 62, 507-509 (1974)) which, if resolved, could have an impact on the way 5-FU is used clinically.

Table 2 sets forth the structures of the parent drug and prodrugs tested in this example. Equations 1 and 2 depict the formation of the prodrugs. Equation 3 depicts the mechanism of the hydrolysis of the prodrugs. Note that for the sake of convenience in Example 8 the definition of R and $R^1$ have different meanings than elsewhere and that the numbering of the compounds is consistent only within Example 8.

TABLE 2

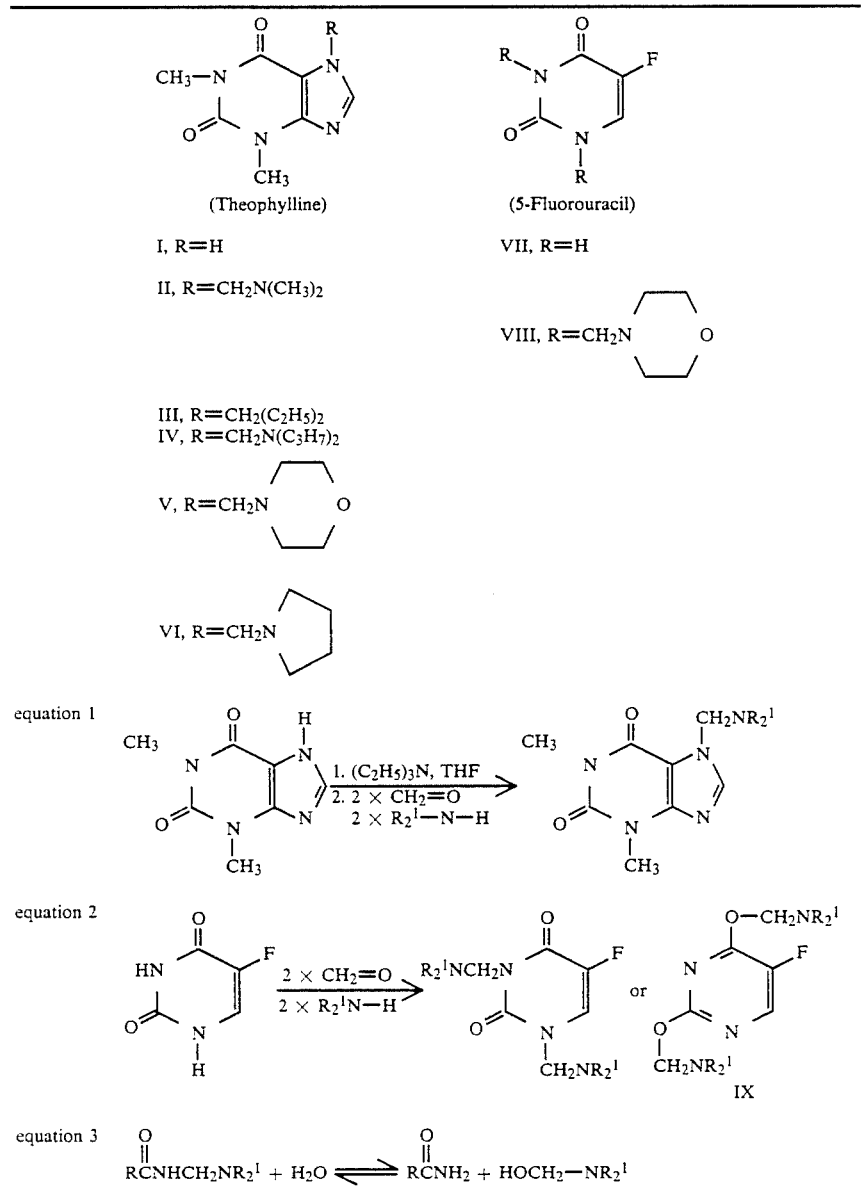

The hairless mice that were used were female SKH-hr-1 from Temple University Skin and Cancer Hospital. The Franz diffusion cells were obtained from Crown Glass Company, Somerville, N.J. TLC were run on Brinkman Polygram Sil G/UV 254. MP (corrected) were taken with a Thomas-Hoover Capillary apparatus.

NMR spectra were recorded on a Varian T-60, IR spectra on a Beckman Accu Lab 1 spectrophotometer and UV spectra on a Beckman model 25 spectrophotometer. Microanalyses were obtained from Atlantic Microlab Inc., Atlanta, GA. 5-Fluorouracil and theophylline were obtained from Sigma while the amines, propylene glycol (PG), and formaldehyde were purchased from Aldrich. The bulk solvents were obtained from Fisher. The isopropyl myristate (IMP) was obtained from Givaudan, Clifton, N.J. The water bath used was a Fisher model 80 circulator bath.

THE PREPARATION OF 1,3-BIS(4'-MORPHOLINYL)METHYL-5-FLUOROURACIL (VIII)

Morpholine (0.44 g, 0.005 mole) was added to 0.4 g (0.005 mole) of 37% $H_2C=O$ in water and diluted with tetrahydrofuran (5 ml). The solution was then allowed to react with 0.33 g (0.0025 mole) of 5-FU (5-fluorouracil); the 5-FU gradually went into solution. After 16 hr the solution was diluted with acetone (20 ml), and was concentrated in vacuo. This process was repeated twice then the residue was dried in a desiccator overnight. The residue (0.60 g, 73% yield, mp 128°–131°) exhibited NMR and IR spectra consistent with the desired product VIII and gave the correct elemental analyses: $^1$H NMR (CDCl$_3$) δ7.4 (d, J=6 Hz, 1, CH=C), 4.93 (s, 2, N—CH$_2$—N), 4.50 (s, 2, N—CH$_2$—N), 3.8–3.45 (m, 8, C—CH$_2$—O) and 2.8–2.45 (m, 8, C—CH$_2$—N) (C=O); UV (CH$_3$OH) max 267 nm (ε=6.45×10$^3$ 1/mole); IR (KBr) 1710 and 1650 cm$^{-1}$ (S) (C=O).

Anal. Calcd. for $C_{14}H_{21}FN_4O_4$: C, 15.24; H, 6.44. Found: C, 51.12; H, 6.45.

The crude product could be triturated with ether to give a 56% recovery of the desired product (mp 137°–139°) which was identical with the analytically pure, crude product by NMR and IR spectroscopy. The IR spectrum of the crude product did not contain any N—H absorptions.

THE PREPARATION OF DERIVATIVES OF THEOPHYLLINE.

The reactions were run on 0.90 g (0.005 mole) of theophylline. The theophylline was treated first with 0.50 g (0.005 mole) of triethylamine then with 10 ml of tetrahydrofuran containing 0.01 mole of the appropriate secondary amine and 0.81 g (0.01 mole) of 37% $H_2C=O$ in water. The reactions were allowed to stir at room temperature for 3 hr, then they were diluted with 150 ml of CH$_2$Cl$_2$. The CH$_2$Cl$_2$ layers were separated, dried over Na$_2$SO$_4$ and concentrated in vacuo to give either oils or solids. These crude products were subsequently triturated with ether or petroleum ether and the products were filtered and dried to give the following derivatives.

7-(Dimethylamino)methyltheophylline (II): 1.05 g, mp 121°–123°, 89% yield from petroleum ether; IR (KBr) 3130 cm$^{-1}$ (M) (C13 H), 1710 and 1665 cm$^{-1}$ (S) (C=O); $^1$NMR (CDCl$_3$) δ63 (s, 1, N=CH—N), 5.15 (s, 2, N—CH$_2$—N), 3.6 and 3.4 (two s, 6, O=CN—CH$_3$) and 2.37 (s, 6, CH$_3$—N); UV (CH$_3$OH) max 273 nm (ε=9.24×10$^3$ 1/mole).

Anal. Calcd. for $C_{10}H_{15}N_5O_2$: C, 50.62: H, 6.37. Found: C, 50.55; H, 6.37.

7-(Diethylamino)methyltheophylline (III): 1.20 g, mp 122°–124°, 90% yield from petroleum ether [lit. (Burckhalter and Dill, J. Org. Chem., 24, 562 (1959) mp 110° in 38% yield or lit. (Rida et al, Pharmazie, 34, 214 (1979) mp 114°–115° in 88% yield]; IR (KBr) 3130 cm$^{-1}$ (M) (C—H), 1710 and 1665 cm$^{-1}$ (S) (C=O); $^1$H NMR (CDCl$_3$) δ 7.66 (s, 1, N=CH—N), 5.33 (s, 2, N—CH$_2$N), 3.6 and 3.4 (two s, 6, O=C—N—CH$_3$) and 2.71 (q, 4, J=7 Hz, N—CH$_2$CH$_3$) and 1.05 (t, 6, J=7 Hz, N—CH$_2$CH$_3$); UV (CH$_3$OH) max 273 nm (ε=9.56×10$^3$ 1/mole).

Anal. Calcd. for $C_{12}H_{19}N_5O_2$:C, 54.32; H, 7.22; Found: C, 54.15; H, 7.24.

7-(Dipropylamino)methyltheophylline (IV): 1.33 g, mp 72°–73°, 90% yield from petroleum ether; IR (KBr) 3130 cm$^{-1}$ (M)(C—H), 1705 and 1665 cm$^{-1}$ (S) (C=O); $^1$H NMR (CDCl$_3$) δ7.63 (s, 1, N=CH—N), 5.27 (s, 2, NCH$_2$N), 3.6 and 3.4 (two s, 6, O=C—N—CH$_3$), 2.6 (t, 4, J=8 Hz; NCH$_2$—CH$_2$—CH$_3$), 1.8–1.2 (m, 4, N—CH$_2$CH$_2$CH$_3$) and 0.9 (t, 6, J=6 Hz, N—CH$_2$CH$_2$CH$_3$); UV (CH$_3$OH) max 273 nm (ε=9.29×10$^3$ 1/mole).

Anal. Calcd. for $C_{14}H_{23}N_5O_2$:C, 57.32; H, 7.90. Found: C, 57.17; H, 7.95.

7-(4'-Morpholinyl)methyltheophylline (V): 1.13 g, mp 175°–178°, 80% yield from absolute ethanol [lit. (Burckhalter and Dill, supra) mp 177° in 92% yield]; IR (KBr) 3130 cm$^{-1}$ (M) (C—H), 1705 and 1660 cm$^{-1}$ (S) (C=O); $^1$H NMR (CDCl$_3$) δ7.57 (s, 1, N=CH—N), 5.2 (s, 2, N—CH$_2$—N), 3.6 and 3.4 (two s, 6, O=C—N—CH$_3$), 3.8–3.6 (m, 4, CH$_2$—O) and 2.8–2.55 (m, 4, N—CH$_2$); UV (CH$_3$OH) max 273 nm (ε=9.58×10$^3$ 1/mole).

7-(Pyrrolidyl)methyltheophylline (VI): 0.85 g, mp 114°–115°, 65% yield from ether [lit. (Burkhalter and Dill, supra) mp 108° in 61% yield]; IR (KBr) 3130 cm$^{-1}$ (M) (C—H), 1710 and 1660 cm$^{-1}$ (S) (C=O); $^1$H NMR (CDCl$_3$) δ7.60 (s, 1, N=CH—N), 5.3 (s, 2, N—CH$_2$—N), 3.57 and 3.37 (two s, 6, O=C—N—CH$_3$), 2.85–2.5 (m, 4, N—CH$_2$) and 2.0–2.55 (m, 4, CH$_2$—CH$_2$—N); UV (CH$_3$OH) max 273 nm (ε=9.49×10$^3$ 1/mole).

Anal. Calcd. for $C_{12}H_{17}N_5O_2$: C, 54.74; H, 6.51. Found: C, 54.65; H, 6.53.

DETERMINATION OF DELIVERY OF DRUGS THROUGH HAIRLESS MOUSE SKIN BY PRODRUGS AND THEIR PARENT DRUGS

Full thickness dorsal skin of 12–14 week-old female hairless mice was used. The mice were sacrificed by cervical dislocation. The excised skin was gently scraped to remove fat and visceral debris then gently secured over the diffusion cells with a rubber gasket. The receptor side of the cell (20 ml) was filled with pH 7.4 isotonic phosphate buffer containing 0.03% formaldehyde (1 ml of 37% $H_2C=O$ in 1000 ml water) and was stirred magentically. The temperature of the cells was maintained at 32° C. with a water bath.

Before the suspensions or solutions of the drugs or prodrugs were applied to the membranes, background UV absorptions due to leaching of UV absorbing material from the skin into the receptor phases were determined for each cell by allowing the skin to be in contact with the receptor phase, and monitoring the UV spectra of the receptor phases until stable spectra were obtained. This usually took from 2 to 4 hr. This absorption was then subtracted from the total absorption observed during the course of the diffusion run to give the absorption due to theophylline at 275 nm or 5-fluorouracil at 270 nm.

All the suspensions or solutions were prepared by sonicating mixtures of the drug or prodrugs in the appropriate solvent in sealed flasks for 3 hr. The sealed solutions or suspensions that resulted were allowed to sit at room temperature for 24 hr, then they were briefly (15 sec.) vortexed and 0.50 ml samples were removed and applied to the membranes (area=4.9 cm$^2$). After an additional 24 hr the remaining sealed suspensions of the prodrugs were filtered, the filtrates and residues were analyzed by inspection of their NMR spectra and TLC to determine if any decomposition of the prodrugs had taken place (none had), and the filtrates were analyzed by UV spectroscopy to determine if the amount of prodrug still in solution corresponded to the solubilities determined in separate experiments (they did). The filtrates were analyzed neat while the residues were dissolved in CDCl$_3$ and the spectra were analyzed for the appearance of the C$_8$—H absorption of theophylline at $\delta 7.77$ and the C$_6$—H absorption of 5-FU at $\delta 7.7$. TLC analyses were run using ether as the eluents. The remaining suspensions of the parent drugs were also filtered and the filtrates were analyzed by UV spectroscopy to determine if the amount of drug still in solution corresponded to the solubilities determined in separate experiments (they did).

After the suspensions or solutions of the drugs or prodrugs were applied to the membranes, samples (3 ml) were taken of the receptor phases at 3, 6, 9, 12 and 24 hr. The receptor phases were immediately replaced with 3 ml of the buffer solution and the samples were analyzed by UV spectroscopy within 0.5 hr.

TLC analyses of the receptor phases showed only the parent drugs were present, and when samples of the receptor phases were made basic the UV spectra underwent a shift of the UV max to longer wavelengths which is characteristic of the N-unsubstituted parent heterocycles. NMR spectroscopy also showed that the derivatives immediately reverted to their parent compounds in water. NMR spectra of the prodrugs in DMSO-d$_6$ showed that, upon addition of water to the NMR samples, there was an immediate loss of the N—CH$_2$—N absorptions in the spectra; no hydroxymethyl N—CH$_2$—OH absorptions ($\delta 5.6$ for theophylline and $\delta 5.2$, 5.1 for 5-FU) were observed.

Three diffusion cells were used for each diffusion cell run in which one each of parent drug in IPM, parent drug in PG, and prodrug in IPM were tested. Thus, during each run the first diffusion cell had parent drug in IPM, the second had parent drug in PG, and the third had the prodrug in IPM applied to the mouse skin membranes, and each combination of parent drug or prodrug in vehicle was run three times.

DETERMINATION OF SOLUBILITIES

The solubilities in the solvents (see Table 3) were determined in two ways. First, an excess of the drug or prodrug in the solvent was sonicated for 3 hr then allowed to sit at room temperature for 24 hr before it was filtered and the filtrate was analyzed by UV spectroscopy. Second, an excess of the drug or prodrug was stirred in the solvent for 24 hr, allowing the suspension to sit at room temperature for 24 hr, then filtering the suspension. All solubilities were determined in triplicate at least, and were reproducible within $\pm 3\%$ under the conditions that they were determined. The neat IPM filtrates were also analyzed by NMR spectroscopy by running each spectrum of each filtrate under exactly the same conditions and comparing the average of five integrations of the C$_8$—H absorptions due to the derivatives (the C$_8$—H for theophylline was not observable because of the low solubility of theophylline); this gave comparative solubilities of the derivatives in IPM and verified that the prodrugs were intact in the IPM solutions.

Analysis by UV and NMR spectroscopy of samples of solutions or suspensions of drugs or prodrugs used in diffusion cells experiments gave the same solubilities as these solubility determinations.

The derivatives are not stable in the presence of water. This result is consistent with results obtained using equations developed for the hydrolysis of Mannich bases and the pKas of the parent compounds (5-FU, pKas 8.0 and 13.0; theophylline, pKa 8.6) which suggested t $\frac{1}{2}$ values of about $1.3 \times 10^{-5}$ min (N—3) and 7 min (N—1) for the 5-FU (VIII), and $5 \times 10^{-8}$ min for the theophylline (VI) derivatives. NMR experiments also supported the low stability of the derivatives in water. Solutions of the bases were prepared in dry DMSO-d$_6$ and then D$_2$O was added stepwise to the solutions. As soon as the first drops of D$_2$O were added the ratio of the N—CH$_2$—N absorptions to the C$_8$—H or C$_6$—H absorptions in theophylline or 5-FU, respectively, immediately decreased until a new equilibrium was obtained between the amide (or imide) plus the carbinolamine (formaldehyde plus amine), and the base plus water (Equation 3). NMR spectra of the bases in D$_2$O showed that immediate and complete decomposition had occurred, as determined by the complete loss of the N—CH$_2$—N absorptions. Similar, decomposition of the bases was also observed in other protic solvents such as methanol and propylene glycol. Thus, the base prodrugs are chemically labile and do not require enzymatic assistance to regenerate the parent drugs under the conditions of the diffusion cell experiments.

On the other hand, the stability of the bases in IPM was variable. On the basis of analyses of NMR spectra of the solid phases and the solutions, derivatives II, V, VI and VIII were found to be stable in IPM either in the solid phase or in solution 24 hours after they had been sonicated for 3 hours. Under those conditions derivatives III and IV were stable in solution but the IPM insoluble material was theophylline. This result is likely due to decomposition in solution of the base followed by precipitation of theopylline since theophylline is so much less soluble in IPM than any of the derivatives. Support for such an interpretation follows from the fact that dissolution of the bases by stirring overnight instead of sonication resulted in higher observed solubilities for III and IV but not for II. In the case of III, the analysis of the NMR spectrum of the IPM insoluble portion showed only the prodrug was present while in the case of IV mostly theophylline remained.

When the IPM filtrates, which were used to determine the IPM solubilities of II and III were exposed to atmospheric moisture at room temperature for two days, 50–80% decomposition of the base prodrugs in solution occurred and precipitation of theophylline resulted as determined by analysis of NMR spectra of the solutions and precipitates. The IPM solutions of the other bases eventually decomposed 1–10% upon prolonged exposure (two weeks) to atmospheric moisture. Although no quantitative data were determined, the qualitative order of stability of the theophylline bases to exposure to atmospheric moisture in IMP solution was V=VI>>IV>III>II, as determined by analysis of NMR spectra of their IPM solutions and precipitates from IPM solutions.

The trend in the IPM solubility data generated by UV for the bases of theophylline by either method in Table 3 was found to be consistent with the trend observed by analysis of the NMR spectra of the neat IPM solutions of the prodrugs immediately after filtration, i.e., III->IV>VI>II>V. The fact that there was agreement between the solubility data obtained for II by all three methods suggests that for thermally stable bases either method in Table 3 can be used to determine solubilities. Two additional trends in the solubility data were also apparent. First, the relatively polar 5-FU and theophylline molecules were quite soluble in protic solvents such as water and propylene glycol but were relatively insoluble in IPM (as expected). Second, the base prodrugs exhibit significantly improved water and lipid (IPM) solubilities. The only derivative for which an approximation of P could be obtained was V. The water solubility of V was very close to 100 mg/ml (the water solubilities of the other derivatives appear to be much higher); hence the approximate P value was 0.013 for V compared to an approximate P value of 0.0114 for theophylline.

DIFFUSION STUDIES

One derivative each of theophylline and 5-FU was chosen for study in diffusion cell experiments using hairless mouse skin. The pyrrolidylmethyl derivative VI of theophylline was chosen for study because it was the most lipid soluble of the derivatives that were thermally stable and relatively stable to atmospheric moisture. The bis-(4'-morpholinyl)methyl derivative VIII of 5-FU was chosen for study because it was stable and it was the best characterized derivative.

The diffusion data (Table 4, 5 and FIGS. 1 and 2) show two trends. First, increased solubility of the drug in the vehicle is not the most important consideration in choosing a vehicle for topical delivery. With both I and VII, increased solubility of the drug in the vehicle chosen actually led to a retardation in rate of delivery and an increase in lag time due to a greater attachment of the vehicle to the drug and hence less favorable partitioning from the vehicle to the skin. Thus, IPM appears to be a much better vehicle for delivery of polar drugs than PG. Second, the prodrugs of the invention appear to be the most effective prodrugs that have been developed for the delivery of theophylline and 5-FU through skin.

In order to support the second conclusion, it was determined that for the parent drugs the diffusion data that were generated in this study were consistent with previous studies using different cells. The previous study of prodrugs of theophylline (Sloan et al, supra), presented data for the delivery of theophylline in IPM for 3, 6, 9 and 12 hr from which a flux of $1.72 \pm 0.13 \times 10^{-2}$ mg/cm$^2$.hr (r=0.999) could be determined. The flux of $2.85 \pm 1.79 \times 10^{-2}$ mg/cm$^2$.hr (r=0.982) obtained in this study was not significantly different from the previously determined flux (p<0.5>0.2), thus suggesting that the results of the two studies are consistent with each other.

The base VI was about 6.9 times (19.5/2.85) more effective than theophylline in delivering theophylline while the 7-(hydroxymethyl)theophylline prodrug, which was the best prodrug for the delivery of theophylline previously described ($11.1 \times 10^{-2}$ mg/cm$^2$.hr) was only about 6.5 times more effective than theophylline (11.1/1.72). In addition, the best acyloxymethyl prodrug derivative [the 7-butyryloxymethyl)theophylline derivative, $7.25 \times 10^{-2}$ mg/cm$^2$.hr] was only 4.2 times (7.25/1.72) better than theophylline in delivering theophylline from IPM. Therefore, the base VI is qualitatively comparable to the best prodrug of theophylline previously described and is significantly better than the best acyloxyalkyl derivative.

Although diffusion data for 3, 6, 9 and 12 hr have been used in comparison of this work with the previous work on theophylline, when the 24 hr data of this study was included in the calculation (see FIG. 1) a flux of $4.32 \pm 2.58 \times 10^{-2}$ mg/cm$^2$.hr was obtained (using 9, 12 and 24 hr data) with a lag time of 5.3 hr. No data for 24 hr was available from the previous study so a comparison including the 24 hr flux data was not possible. The flux for the Mannich base of theophylline from 12 to 24 hr decreased considerably as well over 42% of the total applied theophylline had been delivered at 24 hr.

The diffusion cell data previously reported for the delivery of 5-FU from PG (Mollgaard et al, supra), were analyzed and a flux of $7.8 \times 10^{-4}$ mg/cm$^2$.hr with a lag time of 17 hr was calculated. The present study agrees with that study in that no 5-FU was observed in the receptor phase until the 24 hr samples. When the values for the flux and lag time calculated from the data of Mollgaard et al, were used to calculate a theoretical 24 hr value for 5-FU diffused under the conditions of the present study [7 hr (24 hr-17 hr lag time) and 4.9 cm$^2$=area of membrane], a value of 0.015 mg of 5-FU diffused at 24 hr was obtained. In view of the high standard deviations observed in these experiments and the fact that one value was obtained using human, the other using hairless mouse skin this calculated value was probably not significantly different from the 24 hr value that was actually observed (see Table 5). Thus, the present study of delivery of 5-FU appears to be consistent with the observations of Mollgaard et al, supra.

When the data for flux in Table 4 were used, the prodrug for 5-FU (VIII) was 5.5 times more effective than 5-FU in delivering 5-FU from IPM and 40 times more effective than 5-FU delivery from PG through mouse skin. When the data for the diffusion of the best prodrug of 5-FU (1-butyryloxymethyl derivative) described in Mollgaard et al, supra, were used to calculate a flux for that prodrug, a flux of $17.2 \times 10^{-4}$ mg/cm$^2$.hr was obtained. Thus, the acyloxymethyl prodrug of 5-FU was only 2.2 times better than 5-FU in delivering 5-FU, and the prodrug derivative of the invention is much more effective in delivering 5-FU than the best acyloxymethyl derivative reported.

The prodrug derivatives of theophylline and 5-FU as well as the hydroxymethyl derivatives of theophylline are significant compared to other prodrugs of amides and imides which have been designed to enhance delivery of their parent drugs through skin because they exhibit enhanced water as well as enhanced lipid solubilities. These more water soluble (polar) prodrugs are also more effective in improving topical delivery than prodrugs that have been designed to incorporate only lipid solubilizing groups into the structure of the parent drugs. Although this result should not be surprising in view of the fact that skin and other biological membranes present lipid-water (biphasic) barriers to absorption, increased water solubility had not usually been a design factor when developing prodrugs (especially of polar heterocyclic drugs) for improved topical delivery. Regardless, then, of the molecular mechanism by which the present result is accomplished, increased water as well as lipid solubility should be a design goal in the development of prodrugs for improved topical delivery, and the prodrugs of the invention are attractive candidates for accomplishing that goal, especially since they are chemically labile and do not require enzymatic assistance to regenerate the parent drugs under protic conditions.

TABLE 3

Solubilities of Prodrugs and Parent Drugs in Selected Solvents

| Drug or Prodrug | Water | Solubility (mg/ml) IPM[d] | PG[d] |
|---|---|---|---|
| I, Theophylline | 8.3[a] | 0.095[c] | 16.2[c] |
| II, R=CH$_2$—N(CH$_3$)$_2$ | >100[b] | 7.6[c,e] | |
| III, R=CH$_2$—N(C$_2$H$_5$)$_2$ | >100[b] | 32.5[e] | |
| IV, R=CH$_2$N(C$_3$H$_7$)$_2$ | >100[b] | 27.6[e] | |
| V, 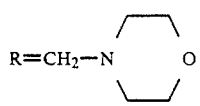 R=CH$_2$—N⟨ ⟩O | >100[b] | 1.3[c] | |
| VI, R=CH$_2$—N⟨ ⟩ | >100[b] | 10.7[c] | |
| VII, 5-Fluorouracil | 26.2[c] | 0.0044[c] | 15.1[c] |
| VIII, R=CH$_2$—N⟨ ⟩O | >100[b] | 11.8[c] | |

[a] The Merck Index, Windholz, M., Ed, 9th ed, Merck and Co. Inc., Rahway, N.J., 1976.
[b] Values obtained by adding 1.0 ml of water (pH 7.0) to 100 mg of Mannich base and sonicating the mixture for 10 sec. This is not an accurate measure of solubilities due to the very rapid decomposition of the Mannich bases in water (Equation 3). Thus, the apparent increases in the solubilities of the prodrugs is probably due to the ability of the amines that are formed during the decomposition of the prodrugs to ionize the parent drugs that are also formed during the decomposition of the prodrugs.
[c] Values obtained by analysis of suspensions sonicated for 3 hr.
[d] IPM = isopropyl myristate, PG = propylene glycol.
[e] Values obtained by analysis of suspensions stirred at room temperature for 24 hr.

TABLE 4

Comparison of Delivery of Theophylline (TH) Through Hairless Mouse Skin by VI and Theophylline

| Drug or Prodrug (Vehicle) | | mg Present as Parent Drug in Solution in Donor Phase. | mg (± S.D., N = 3) Present as Parent Drug in Receptor Phase after 12 hr. | Flux (mg/cm$^2$ · hr ± S.D., N = 3) | Lag Time (hr) |
|---|---|---|---|---|---|
| I, Theophylline[a] | (IPM)[b] | 0.047 | 1.41 ± 0.89 | 2.85 ± 1.79 × 10$^{-2e}$ | 2.6 |
| I, Theophylline[a] | (PG)[c] | 8.1 | 0.024 ± 0.023 | 1.29 ± 0.64 × 10$^{-3f}$ | 7.7 |
| VI, TH-7-CH$_2$N⟨ ⟩[a] | (IPM)[b] | 3.7[d] | 9.17 ± 0.98 | 19.5 ± 0.18 × 10$^{-2e}$ | 2.2 |

[a] 0.50 ml of a 0.36 M suspension, or the equivalent of 32.4 mg of theophylline applied.
[b] isopropyl myristate.
[c] propylene glycol.
[d] 5.4 mg of prodrug in solution.
[e] calculated based on linear regression analysis of data for 3, 6, 9 and 12 hr.
[f] determined from only 12 and 24 hr data in two runs and 9, 12 and 24 hr data in the third run.

TABLE 5

Comparison of Delivery of 5-Fluorouracil (5-FU) Through Hairless Mouse Skin by VIII and 5-Fluorouracil

| Drug or Prodrug (Vehicle) | | mg Present as Parent Drug in Solution in Donor Phase. | mg (± S.D., N = 3) Present as Parent Drug in Receptor Phase after 12 hr. | Flux (mg/cm$^2$ · hr S.D., N = 3) | Lag Time (hr) |
|---|---|---|---|---|---|
| VII, 5-Fluorouracil[a] | (IPM)[c] | 0.0022 | 0.25 ± 0.023 | 5.56 ± 3.55 × 10$^{-3g}$ | 2.7 |
| VII, 5-Fluorouracil[b] | (PG)[d] | 2.6 | 0.011[f] | 7.8 × 10$^{-4h}$ | 17[h] |
| VIII, 5-FU-1,3-CH$_2$N⟨ ⟩O[a] | (IPM)[c] | 2.33[e] | 1.59 ± 0.13 | 3.0 ± 0.14 × 10$^{-2g}$ | 0.8 |

[a] 0.50 ml of a 0.04M suspension, or the equivalent of 2.6 mg of 5-FU applied.
[b] 0.5 ml of a 0.04M solution, or the equivalent of 2.6 mg of 5-FU applied.
[c] isopropyl myristate.
[d] propylene glycol.
[e] 5.9 mg of prodrug in solution.
[f] 24 hr data.
[g] calculated based on linear regression analysis of data for 3, 6, 9 and 12 hr.
[h] calculated from data in the literature (Mollgaard, et al., 1982).

In the drawing, FIG. 1 represents a plot of the delivery over time of theophylline through hairless mouse skin by theophylline in IPM (●) and by the prodrug VI in IPM (▲). FIG. 2 represents a plot of the delivery over time of 5-FU through hairless mouse skin by 5-FU in PG (■), by 5-FU in IPM (●) and by the prodrug VIII in IPM (▲).

EXAMPLE 9

The procedure of Example 8 was employed to determine the delivery of 9-(N-diethylamino)methyl-6-mercaptopurine (prepared according to Example 6) across hairless mouse skin. The results are set forth in Table 6.

TABLE 6

Delivery of 6-Mercaptopurine (6-MP) Through Hairless Mouse Skin by 6-Mercaptopurine (I) and by 9-(N-diethylamino)methyl-6-mercaptopurine (II).

| Compound (Vehicle) | % of applied 6-MP[a] delivered after 12 hr | Lag time (hr) |
|---|---|---|
| I (PG) | 0.06 | 8 |
| I (IPM) | 0.06 | 8 |
| II (IPM) | 2.5 | 2 |

[a]0.5 ml of a 0.04 M suspension applied to a 4.9 cm$^2$ area of skin.

EXAMPLE 10

The following examples illustrate methods for preparing various derivatives of cytosine, 5-fluorouracil and 5-fluorocytosine (5-FC) according to the invention and their effectiveness as prodrugs for enhanced delivery of cytosine and 5-FC across topical membranes.

THE REACTION OF CYTOSINE WITH EXCESS FORMALDEHYDE AND A SECONDARY AMINE

To 0.55 g (0.005 mole) of cytosine was added 2.38 g (0.03 mole) of 37% aqueous formaldehyde; the suspension was stirred until a clear solution had formed. A secondary amine (0.03 mole) was slowly added to the stirred solution. After 24 hours, a white solid precipitated. The reaction mixture was triturated with tetrahydrofuran (when the amine was morpholine) or with ether (when the amine was piperidine) to yield the desired product:

Bis-N$^4$, 1-(1'-piperidinyl)methylcytosine (VIII). mp 192°–194° [lit. 195°–196°], yield 90.9%; IR (KBr) 3280 cm$^{-1}$ (M) (N—H), 1665 (shoulder, S) and 1643 (S) and 1600 (S) (C=O and C=N); $^1$H NMR (CDCl$_3$) δ 7.38 (d, 1, J=8 Hz, 6—CH), 4.50 (s, 2, N—CH$_2$—N), 4.40–3.87 (m, 2, NH—CH$_2$—N), 2.80–2.23 (m, 8, CH$_2$—N—CH$_2$), 1.87–1.20 (m, 12, C—CH$_2$); UV (CH$_3$CN) max 277 nm ($\epsilon$=8.34×10$^3$ 1/mole) max 246 nm ($\epsilon$=7.92×10$^3$ 1/mole), UV (HCl) max 289 nm ($\epsilon$=1.09×10$^4$ 1/mole) and UV (NaOH) max 277 nm ($\epsilon$=7.77×10$^3$ 1/mole) max 244 nm ($\epsilon$=7.72×10$^3$ 1/mole).

Bis-N$^4$, 1-(4'-morpholinyl)methylcytosine (IXa). mp 191°–192° [lit. 192°–193° C.], yield 78%; IR (KBr) 3280 cm$^{-1}$ (S) (N—H), and 1665 (shoulder, S) and 1645 (S) and 1610 (M) (C=O and C=N); $^1$H NMR (DMSO-d$_6$) δ7.50 (d, 1, J=8 Hz, 6—CH), 5.70 (d, 1, J=8 Hz, 5—CH), 4.47 (s, 2, N—CH$_2$—N), 2.70–2.30 (m, 8, CH$_2$—O—CH$_2$); UV (CH$_3$CN) max 277 nm ($\epsilon$=8.34×10$^3$ 1/mole) max 249 nm ($\epsilon$=8.44×10$^3$ 1/mole), UV (HCl) max 290 nm ($\epsilon$=1.24×10$^4$ 1/mole) and UV (NaOH) max 277 nm ($\epsilon$=8.35×10$^3$ 1/mole) max 248 nm ($\epsilon$=8.29×10$^3$ 1/mole).

REACTION OF CYTOSINE WITH EXCESS PARAFORMALDEHYDE AND A SECONDARY AMINE

To 6.0 g (0.02 mole) of paraformaldehyde in 40 ml of methylene chloride was added 0.02 mole of the appropriate secondary amine. The suspension was stirred until a solution formed (2–24 hours), at which time 0.55 g (0.005 mole) of cytosine was added. This suspension was stirred overnight and the solution that resulted was dried over sodium sulfate, filtered, and the filtrate was concentrated in vacuo. The residue was triturated to yield the desired adducts with cytosine:

Bis-N$^4$, 1-(dimethylamino)methylcytosine hydrate (X): 126°–128°, 48% yield from ether/petroleum ether (1:1); IR (KBr) 3210 (M) and 3100 cm$^{-1}$ (W) (NH and OH), 1665 (S) and 1635 (S) (C=O and C=N); $^1$H NMR (CDCl$_3$) δ7.19 (s, 1, J=7 Hz, 6—CH), 5.76 (d, 1, J=7 Hz, 5—CH), 5.97–5.60 (m, 1, NH), 4.47 (s, 2, N—CH$_2$—N), 4.30–3.90 (m, 2, NH—CH$_2$—N) and 2.35 (s, 12, N—CH$_3$); UV (CH$_3$CN) max 276 nm ($\epsilon$=8.56×10$^3$ 1/mole) max 246 nm ($\epsilon$=8.56×10$^3$ 1/mole) and UV (NaOH) max 276 nm ($\epsilon$=8.48×10$^3$ 1/mole) max 244 nm ($\epsilon$=9.86×10$^3$ 1/mole).

Anal. Calcd. for C$_{10}$H$_{19}$N$_5$O 0.33 H$_2$O: C, 51.93; H, 8.56. Found: C, 51.92; H, 8.17.

Bis-N$^4$, 1-(4'-morpholinyl)methylcytosine hydrate (IXb): mp 185°–187°, 53% yield from ether; IR (KBr) 3260 (M) and 3130 cm$^{-1}$ (W) (NH and OH), 1660 (S) and 1635 (S) (C=O and C=N); $^1$H NMR (CDCl$_3$) δ7.25 (d, 1, J, 7 Hz, 6—CH), 5.68 (d, 1, J=7 Hz, 5—CH), 6.12–5.52 (m, 1, NH), 4.52 (s, 2, N—CH$_2$—N), 4.38–3.92 (m, 2, NH—CH$_2$—N), 3.82–3.50 (m, 8, CH$_2$—O—CH$_2$) and 2.78–2.32 (m, 8, CH$_2$—N—CH$_2$); UV (CH$_3$CN) max 277 nm ($\epsilon$=8.34×10$^3$ 1/mole) max 249 nm ($\epsilon$=8.44×10$^3$ 1/mole), UV (HCl) max 290 nm ($\epsilon$=1.24×10$^4$ 1/mole) and UV (NaOH) max 277 nm ($\epsilon$=8.35×10$^3$ 1/mole) max 248 nm ($\epsilon$=8.29×10$^3$ 1/mole).

Anal. Calcd for C$_{14}$H$_{23}$N$_5$O$_3$ 0.25 H$_2$O: C, 53.58; H, 7.54. Found: C, 53.58; H, 7.43.

Bis-N$^4$, 1-(4'-methyl-1'-piperazinyl)methylcytosine hydrate (XI): mp 186°–188°, 35% yield from ether; IR (KBr) 3260 (M) and 3110 cm$^{-1}$ (W) (NH and OH), 1660 (S) and 1630 (S) (C=O and C=N); $^1$H NMR (CDCl$_3$) δ7.28 (d, 1, J=7 Hz, 6—CH), 5.62 (d, 1, J=7 Hz, 5—CH), 6.02–5.38 (m, 1, N—H), 4.52 (s, 2, N—CH$_2$—N), 4.42–3.85 (m, 2, NH—CH$_2$—N), 2.85–2.52 (broad s, 8, CH$_2$—N—CH$_2$), 2.52–2.33 (broad s, 8 CH$_2$—N(CH$_3$)—CH$_2$) and 2.28 (s, 6, N—CH$_3$); UV (CH$_3$CN) max 276 nm ($\epsilon$=9106×10$^3$ 1/mole) shoulder max 246 nm ($\epsilon$=9.66×10$^3$ 1/mole), UV (HCl) 290 nm ($\epsilon$=9.60×10$^3$ 1/mole) and UV (NaOH) max 276 nm ($\epsilon$=9.09×10$^3$ 1/mole) max 244 nm ($\epsilon$=9.77×10$^3$ 1/mole).

Anal. Calcd for C$_{16}$H$_{29}$N$_7$O 0.5 H$_2$O: C, 55.79; H, 8.78. Found: C, 56.07; H, 8.57.

REACTION OF 5-FLUOROCYTOSINE WITH FORMALDEHYDE AND PIPERIDINE (XIIa).

To 0.39 g (0.003 mole) of 5-fluorocytosine (5-FC) was added 0.97 g (0.012 mole of 37% aqueous formaldehyde, and the suspension was stirred until a clear solution had formed. The 1.02 g (0.012 mole) of piperidine was added, and the reaction mixture was diluted with 10 ml tetrahydrofuran. After 24 hours the suspension was triturated with ether to give bis-N$^4$, 1-(1'-piperidinyl)- methyl-5-fluorocytosine (84%, mp>220° (d)) as a white solid:

IR (KBr) 3220 cm$^{-1}$ (W) (NH), 1685 (M) and 1635 (S) (C=O and C=N); $^1$H NMR (CDCl$_3$) δ 7.40 (d, 1, J=6 Hz, C=CH), 5.82-5.28 (m, 1, N—H), 4.52-4.23 (broad s, 4, N—CH$_2$—N), 2.75-2.38 (m, 8, CH$_2$—N—CH$_2$) and 1.77-1.25 (m, 12, C—CH$_2$); UV (CH$_3$CN) max 289 nm (ε=6.99×10$^3$ 1/mole) max 242 nm (ε=8.15×10$^3$ 1/mole), UV (HCl) max 281 nm (ε=7.92×10$^3$ 1/mole) and UV (NaOH) max 289 nm (ε=6.56×10$^3$ 1/mole) max 244 nm (ε=8.14×10$^3$ 1/mole).

Anal. Calcd for C$_{16}$H$_{26}$FN$_5$O: C, 59.42; H, 8.10; N, 21.66. Found: C, 59.38; H, 8.14; N, 21.63.

REACTION OF 5-FLUOROCYTOSINE WITH EXCESS PARAFORMALDEHYDE AND A SECONDARY AMINE.

To 0.24 g (0.008 mole) of paraformaldehyde in 20 ml of methylene chloride was added 0.008 mole of the appropriate secondary amine. The suspension was stirred until a solution resulted (2-24 hours). 5-fluorocytosine (0.25 g, 0.002 mole) was added to the solution and the suspension that formed was stirred overnight. The solution that resulted was concentrated in vacuo and the residue was triturated twice with ether or a mixture of ether and petroleum ether (1:1). The following N-Mannich bases were obtained:

Bis-N$^4$, 1-(dimethylamino)methyl-5-fluorocytosine hydrate (XIII): mp 136°-138°, yield 46% from ether/petroleum ether (1:1); IR (KBr) 3190 (M) and 3025 cm$^{-1}$ (W) (NH and OH), 1665 (M) and 1615 (S) (C=O and C=N); $^1$H NMR (CDCl$_3$) δ7.37 (d, 1, J=6 Hz, 6—CH), 4.52-4.28 (broad s, 4, N—CH$_2$—N) and 4.03 (s, 12, N—CH$_3$); UV (CH$_3$CN) max 289 nm (ε=6.99×10$^3$ 1/mole) max 243 nm (ε=8.15×10$^3$ 1/mole), UV (HCl) max 282 nm (ε=7.96×10$^3$ 1/mole) and UV (NaOH) max 289 nm (ε=5.63×10$^3$ 1/mole) max 242 nm (ε=7.83×10$^3$ 1/mole).

Anal. Calcd for C$_{10}$H$_{18}$FN$_5$O 0.25 H$_2$O; C, 48.47; H, 7.53. Found: C, 48.29; H, 7.21.

Bis-N$^4$, 1-(diethylamino)methyl-5-fluorocytosine hydrate (XIV): mp 129°-131°, 70% yield from ether; IR (KBr) 3210 cm$^{-1}$ (broad, W) (NH and OH), 1680 (M) and 1630 (S) (C=O and C=N); $^1$H NMR (CDCl$_3$) δ 7.53 (d, 1, J=6 Hz, 6-CH), 5.57-5.17 (m, 1, N—H), 4.63-4.37 (broad 2, 4, N—CH$_2$—N), 2.68 (q, 8, J=7 Hz, N—CH$_2$—CH$_3$) and 1.08 and 1.05 (2 t, 12, J=7 Hz, CH$_2$—CH$_3$); UV (CH$_3$CN) max 289 nm (ε=7.69×10$^3$ 1/mole) max 244 nm (ε=8.82×10$^3$ 1/mole), UV (HCl) max 291 nm (ε=1.16×10$^4$ 1/mole), UV (NaOH) max 289 nm (ε=6.85×10$^3$ 1/mole) max 244 nm (ε=8.67×10$^3$ 1/mole).

Anal. Calcd for C$_{14}$H$_{26}$FN$_5$C 0.25 H$_2$O: C, 55.33; H, 8.62; N, 23.05. Found: C, 55.43; H, 8.69; N, 23.06.

Bis-N$^4$, 1-(1'-pyrrolidyl)methyl-5-fluorocytosine hydrate (XV): mp 140°-142° (foam, d); 85% yield from ether/petroleum ether (1:1); IR (KBr) 3220 cm$^{-1}$ (broad, W) (NH and OH), 1675 (S) and 1645 (S) (C=O and C=N); $^1$H NMR (DMSO-d$_6$) δ 7.72 (d, 1, J=6 Hz, 6-CH), 5.05-4.78 (m, 1, NH), 4.48 (s, 2, N—CH$_2$—N), 4.35-4.10 (m, 2, NH—CH$_2$—N), 2.82-2.32 (m, 8, CH$_2$—N—CH$_2$) and 1.92-1.42 (m, 8, C—CH$_2$); UV (CH$_3$CN) max 289 nm (ε=6.13×10$^3$ 1/mole) max 243 nm (ε=7.22 ×10$^3$ 1/mole), UV (HCl) max 278 nm (ε=7.35×10$^3$ 1/mole), UV (NaOH) max 289 nm (ε=5.70×10$^3$ 1/mole), max 243 nm (ε=9.23×10$^3$ 1/mole).

Anal. Calcd for C$_{14}$H$_{22}$FN$_5$O 0.75 H$_2$O: C, 54.79; H, 7.21; N, 22.78. Found: C, 54.59; H, 7.31; N. 22.45.

Bis-N$^4$, 1-(1'-piperidinyl)methyl-5-fluorocytosine (XIIb): 181°-183°, 83% yield from ether/petroleum ether (1:1) and then ether; IR (KBr) 3220 cm$^{-1}$ (W) (NH), 1685 (M) and 1635 (S) (C=O and C=N); $^1$H NMR (CDCl$_3$) δ 7.40 (d, 1, J- 6 Hz, 6—CH), 5.82-5.28 (m, 1, N—H), 4.52-4.23 (broad s, 4, N—CH$_2$—N), 2.75-2.38 (m, 8, CH$_2$—N—CH$_2$) and 1.77-1.25 (m, 12, C—CH$_2$); UV (CH$_3$CN) max 289 nm (ε=6.99×10$^3$ 1/mole) max 242 nm (ε=8.15×10$^3$ 1/mole), UV (HCl) max 281 nm (ε=7.92×10$^3$ 1/mole) and UV (NaOH) max 289 nm (ε=6.56×10$^3$ 1/mole) max 244 nm (ε=8.14×10$^3$ 1/mole).

Anal. Calcd for C$_{16}$H$_{26}$FN$_5$O: C, 59.42; H,, 8.10; N, 21.66. Found: C, 59.23; H, 8.11.

Bis-N$^4$, 1-(4'-morpholinyl)methyl-5-fluorocytosine hydrate (XVI): mp 154°-156°, 71% yield from ether/petroleum ether (1:1) and then ether; IR (KBr) 3220 cm$^{-1}$ (broad, W) (NH and OH), 1680 (S) and 1630 (S) (C=O and C=N); $^1$H NMR (CDCl$_3$) δ 7.35 (d, 1, J=6 Hz, 6—CH), 5.92-5.39 (m, 1, N—H), 4.58-4.25 (broad s, 4, N—CH$_2$—N), 3.88-3.48 (m, 8, CH$_2$—N—CH$_2$) and 2.82-2.38 (m, 8, CH$_2$—O—CH$_2$); UV (CH$_3$CN) max 289 nm (ε=7.20×10$^3$ 1/mole) max 246 (ε=9.25×10$^3$ 1/mole), UV (HCl) max 282 nm (ε=8.82×10$^3$ 1/mole), UV (NaOH) max 289 (ε=6.70×10$^3$ 1/mole) max 246 nm (ε=9.23×10$^3$ 1/mole).

Anal. Calcd for C$_{14}$H$_{22}$FN$_5$O$_3$ 0.33 H$_2$O: C, 50.44; H, 6.98; N, 21.01. Found: C, 50.30; H, 6.72; N, 21.01.

Bis-N$^4$, 1-(4'-methyl-1'piperazinyl)methyl-5-fluorocytosine hydrate (XVII): mp 163°-165°, 73% yield from ether/petroleum ether (1:1); IR (KBr) 3210 cm$^{-1}$ (broad, W) (NH and OH), 1675 (S) and 1625 (S) (C=O and C=N); $^1$H NMR (CDCl$_3$) δ 7.35 (d, 1, J=6 Hz, 6—CH), 5.95-5.35 (m, 1, N—H), 4.58-4.32 (broad s, 4, N—CH$_2$—N), 2.85-2.57 (m, 8, CH$_2$—N—CH$_2$), 2.57-2.35 (m, 8, CH$_2$—N(CH$_3$)—CH$_2$) and 2.27 (s, 6, N—CH$_3$); UV (CH$_3$CN) max 289 nm (ε=6.49×10$^3$ 1/mole max 245 nm (ε=8.07×10$^3$ 1/mole), UV (HCl) max 2.90 nm (ε=8.46×10$^3$ 1/mole) and UV (NaOH) max 289 nm (ε=6.46×10$^3$ 1/mole) max 245 nm (ε=7.99×10$^3$ 1/mole).

Anal. Calcd for C$_{16}$H$_{28}$FN$_7$O 0.75 H$_2$O; C, 52.37; H, 8.10; N. 26.72. Found: C, 52.32; H, 7.78; N, 26.69.

1,3-Di(piperidylmethyl)-5-fluoruracil: To 0.04 mole of piperidine that was coled with an ice bath was added 0.04 mole of 37% aqueous formaldehyde. After 5 min., 2.5 g (0.019 mole) of 5-fluorouracil was added and the mixture was stirred at room temperature overnight. The mixture was dissolved in 150 ml of dichloromethane. The dichloromethane layer was separated, dried over Na$_2$SO$_4$ and concentrated in vacuo at room temperature. The concentrate was triturated with 5 ml of anhydrous ether overnight, then the suspension was filtered and the residue was dried in vacuo to give 2.2 g (mp 88°-92°) of the desired compound by NMR spectroscopy. The material was repeatedly triturated with small amounts of ether until a white solid with a constant melting point of 96°-98° was obtained: $^1$H NMR (CDCl$_3$) δ 7.48 (d, 1, J=4HZ, 6—H), 4.97 and 4.50 (2s, 4, N—CH$_2$—N), 2.8-2.4 (m, 8,, CH$_2$—N) and 1.8-1.3 (m, 12, CH$_2$—CH$_2$).

1,3-Di(4'-methyl-1'-piperazinylmethyl)-5-fluoracil was prepared in a similar manner to give 2.5 g (mp 116°-120°) of the desired compound whose melting point could be improved to 117°-120°: $^1$H NMR (CDCl$_3$) δ 7.41 (d, 1, J=4 Hz, 6—H), 5.01 and 4.48 (2s, 4, N—CH$_2$—N), 2.9–2.6 (m, 8, CH$_2$—N), 2.6–2.35 (m, 8, CH$_2$—N—CH$_3$) and 2.3 and 2.35 (2s, 6, N—CH$_3$).

DETERMINATION OF HALF-LIVES AND RATES OF HYDROLYSIS.

The hydrolysis of the prodrugs in pH 7.1 phosphate buffer was monitored by UV at 278 nm, by measuring the appearance of 5-FC, or at 268 nm, to measure th appearance of cytosine. The hydrolyses were determined to be first-order by plotting log $(A_t - A\infty)$ versus time. The hydrolyses were then run in triplicate at a constant temperature of 24° and the half-lives and rates of hydrolysis were obtained. For the derivatives an aliquot (0.1 ml) was added to 3 ml of buffer in a cuvette so that the final concentration was between $1 \times 10^{-4} \times 10^5$ M. The addition of acetonitrile did not affect the pH of the buffer, and the pH was checked again after completion of hydrolysis to ensure a constant pH. Hydrolyses at pH 6 and 8 were also performed for the 5-FC derivatives to determine the mechanism of hydrolysis.

DETERMINATION OF LIPID AND AQUEOUS SOLUBILITIES

The lipid solubilities of 5-FC and its derivatives were obtained in isopropyl myristate. Three suspensions of the compound or derivative were stirred for 48 hours; the suspensions were then filtered. The filtrates were then diluted with either methanol, for 5-fluorocytosine, or dry acetonitrile, for the derivatives. The concentration of compound in solution was determined by measuring the UV absorbtion at 278 nm ($\epsilon = 4.98 \times 10^3$ 1/mole) for 5-fluorocytosine or 289 nm for the prodrugs.

The approximate aqueous solubilities were determined by the addition of 100 mg of solid to 1 ml distilled water (pH 5.5). Water was added until all the solid dissolved.

DIFFUSION CELL EXPERIMENTS

The diffusion experiments were performed in triplicate for each compound. Three female, hairless mice were sacrificed by cervical dislocation, and the entire dorsal skin removed by blunt dissection from the underlying tissues. The skins were secured with a rubber gasket to the diffusion cell, with the dermis in contact with the receptor phase. The receptor side of the cell was filled with isotonic phosphate buffer (pH 73 at 32°, 0.05 M, $\mu = 0.15$) with 1% formaldehyde added to inhibit microbial growth. The receptor phase was kept at a constant temperature of 32° and was stirred magnetically.

The skins were placed in contact with the receptor phase for 48 hours to remove any water soluble, UV-absorbing compounds and the receptor phases changed three times during this period. The donor phases were applied as suspensions (0.5 ml, 0.1 M) to the skin surface. The suspensions were stirred for 48 hours prior to application. Samples (3 ml) were removed from the receptor phases at 3, 6, 9, 12, 18, 21 24 30, 36 and 48 hours after application of donor phases. Each sample was replaced by an equal amount of fresh buffer. The UV absorption of the sample was monitored at 278 nm ($\epsilon = 5.94 \times 10^3$ 1/mole) which is the $\lambda$ max of 5-fluorocytosine in this buffer. In order to correct for the 5-FC in the samples that had been removed, 15% of the 5-FC in the previous samples were added to the sample being analyzed. This gave the cumulative amount of 5-FC found in the receptor phase.

After the 48 hours, the remaining donor phase was removed by washing the skin surface with 20 ml of methanol. The washings were combined, diluted to 100 ml with methanol and analyzed by UV spectroscopy (278 nm, $\epsilon = 498 \times 10^3$ 1/mole) to determine the amount of 5-FC remaining in the donor phase (methanol decomposes the prodrugs). The receptor phases were then replaced with fresh buffer and the skins were allowed to remain in contact with the buffer for 24 hours. The receptor phase was then sampled and analyzed by UV spectroscopy to determine the amount of 5-FC remaining in the skin. These last two steps were used to determine the mass balance. This part of the diffusion cell study is termed the first application.

After this last sampling of the receptor phase (amount left in skin), the receptor phase was again changed. The skins were allowed to remain in contact with the buffer for 30 minutes and then a 3 ml sample was removed and analyzed for 5-FC to measure any 5-FC that had leached from the skin. A suspension of theophylline (Th) in propylene glycol (PG) (0.5 ml, 0.4 M) was then applied to each donor phase (the suspension was stirred for 48 hours prior to application). Samples (3 ml) were removed from the receptor phase at 3, 6, 9, 12, 24 and 48 hours after application of the donor phase. The UV absorbance of the samples was monitored a 270 nm ($\epsilon = 1.02 \times 10^4$ 1/mole). The cumulative amount of theophylline in the receptor phase was calculated as described above. This phase of the diffusion cell studies is termed the second application. Student's t-test (one-tailed) was used to test for significant differences between the obtained fluxes.

Several control studies were also performed. Following the same timing as the first application, three hairless mouse skins were allowed to remain in contact with pH 7.3 (at 32°) buffer for a total of 120 hours (nothing applied for the first application), and then Th in PG was applied as before. This was the baseline for the second application. In a second study, three skins were again placed in contact with buffer for 96 hours, washed twice with 10 ml of methanol, and then allowed to come in contact with the buffer for an additional 24 hours. Theophylline in PG was then applied to assess the effect of the methanol wash (used to remove the remaining donor phase from the first application) on the skin's permeability. In the third experiment, three mouse skins were allowed to leach for 48 hours and then 0.5 ml of IPM was added to each cell. After 48 hours, the IPM was washed off by twice rinsing the skins with 10 ml of methanol, and the receptor phase was changed. After 24 hours the receptor phase was again changed and Th in PG was applied. Finally in an attempt to assess the effect of the amine and formaldehyde, three skins were placed in contact with buffer for 48 hous and then a 0.5 ml of a 0.2 M suspension of paraformaldehyde and piperidine in IPM was applied. After 48 hours, the skins were washed twice with 10 ml of methanol and allowed to remain in contact with buffer for an additional 24 hours. The receptor phase was changed and a suspension of Th in PG was added as before.

In order to assess the applicability of these compounds as dermal delivery systems, the effect of human sweat on the delivery of 5-FC from the prodrug XIIb and 5-fluorocytosine (from isopropyl myristate) was studied. A thin layer of sweat (donated by a normal volunteer (KBS), pH 7.0) was applied to the skin surface, then 0.5 ml of the 0.1M suspensions of the compounds in isopropyl myristate were applied as before. Samples were obtained using the same schedule described above. In another experiment, aminomethylating agent was prepared through the reaction of paraformaldehyde (0.008 mole) with piperidine (0.008 mole) in methylene chloride. The solution that resulted was concentrated to an oil. This preformed aminomethylating agent was added to 5-FC (0.004 mole) and was stirred in 4 ml of IPM for 48 hours. Then the mixture of 5-FC and aminomethylating agent was applied to the skins of three mice as in previous experiments.

For each diffusion cell experiment, the cumulative amount, in milligrams, of drug (5-fluorocytosine or theophylline) found in the receptor phase was plotted versus time of sampling. The slopes for each phase of the plotted lines were obtained by linear regression analysis (r>0.990); the slopes were then divided by the surface area of the diffusion cells (4.9 cm$^2$) to obtain a value for flux (J) in mg/cm$^2$/h. The reported fluxes are the average flux of the three diffusion cells. The permeability coefficients were determined by dividing the flux by the compound's solubility in the vehicle (as milligrams of 5-FC per milliliter of vehicle).

EXPERIMENTAL AND CALCULATED SOLUBILITY PARAMETERS

The solubility of 5-fluorocytosine was determined in the following solvents: 1-octanol, dimethylformamide, propylene glycol, ethylene glycol, formamide and two ethylene glycol-formamide mixtures (4:1 and 1:1). The solubility parameter of 5-fluorocytosine was determined using the peak solubility method. The mole fraction solubility of 5-fluorocytosine was compared with the solubility parameter of each solvent. The maximum solubility will occur in the solvent whose solubility parameter is closest to that of 5-fluorocytosine. The solubility parameters of 5-fluorocytosine and its derivatives were also calculated using the group contribution method described above.

STRUCTURE DETERMINATION

Since there are three possible sites of alkylation in cytosine and 5-FC—endocyclic amino groups at positions 1 and 3; exocyclic amino group at position 4—structure determination was necessary. The $^1$H NMR of the aminomethylated adducts suggested that dialkylation had occurred. For example, in the piperidinyl derivative of 5-FC, two resonanances for N—CH$_2$ group were seen ($\delta$4.43 and 4.13 in DMSO-d$_6$). The multiplet ($\delta$4.13) assigned to the N$^4$-methylene group collapsed to a singlet in D$_2$O, suggesting the splitting was caused by an exchangable proton. If the spectra were obtained in CDCl$_3$, only one broad singlet was present that integrated for these 4 methylene protons. When this part of the spectra was expanded, the broad singlet also resolved into a singlet and a multiplet. The assignment of a dialkylated structure to these derivatives correlated with that found in the above described Mannich-type bases with cytosine. The formation of these adducts was also followed by $^1$H NMR. Preformed aminomethylating agent (formed by the reaction of paraformaldehyde with piperdine) was added to 5-FC in DMSO-d$_6$. Alkylation occurred first at the 1-position followed by the slower alkylation of the exocyclic amino group.

The assignment of the N$^4$-position as a site of alkylation has literature precedent. McGhee and Von Hippel found that the reaction of formaldehyde with cytidine formed an N-hydroxymethyl group at the exocyclic amine, and identified the structure by $^1$H NMR. Another group trapped the N$^4$-hydroxymethyl derivative of cytosine with bisulfite and used X-ray crystallography to confirm its structure [McGhee et al, Biochem., 14, 1271–1296 (1978) and Hayatsu et al, Nac. Acid Res., 10, 6281–6293 (1982)].

The remaining singlet was assigned to the 1-position; $^{13}$C NMR was used to confirm this assignment. The spectrum of the bis-adduct of cytosine with formaldehyde and morpholine was obtained in DMSO-d$_6$ and compared with that of cytidine, an 1-substituted cytosine. The spectra were found to be similar. Therefore, these aminomethylated derivatives of 5-FC were assigned bis-N$^4$, 1-alkylated structures.

The structures and M. P. 's of the above described derivatives of cytosine and 5-FC are set forth in Table 7.

TABLE 7

Structures and melting points of the N-Mannich base derivatives of cytosine and 5-fluorocytosine $$\begin{array}{c}NH-CH_2-R\\ \text{(structure)}\\CH_2-R\end{array}$$

| R = $^a$ mp(°C.) | | Cytosine (X = H) compound | mp (°C.) | 5-Fluorocytosine (X = F) compound | mp(°C.) |
|---|---|---|---|---|---|
| —N(CH$_3$)$_2$ | (Me) | X | 126–128 | XIII | 136–138 |
| —N(C$_H$5)$_2$ | (Et) | — | | XIV | 129–131 |
|  | (Py) | —$^b$ | | XV | 140–142(d) |

TABLE 7-continued

Structures and melting points of the N-Mannich base derivatives of cytosine and 5-fluorocytosine

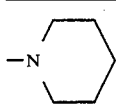

| R =[a] mp(°C.) | | Cytosine (X = H) compound | mp (°C.) | 5-Fluorocytosine (X = F) compound | mp(°C.) |
|---|---|---|---|---|---|
| —N⟨piperidine⟩ | (Pi) | VIII[c] | 192–194 | XIIa[d] XIIb | >220 181–183 |
| —N⟨morpholine⟩O | (Mo) | IXa[c] IXb | 191–192 185–187 | XVI | 154–156 |
| —N⟨piperazine⟩N—CH₃ | (Pz) | XI cytosine | 186–188 320–325(d) | XVII 5-FC | 163–165 295–297 |

[a]These derivatives will be identified hereinafter by number and by the abbreviation for the secondary amine.
[b]Not synthesized.
[c]Synthesized by Method 1, all others synthesized by Method 2.

KINETICS AND MECHANISM OF HYDROLYSIS

The rates of hydrolysis of the Mannich bases of the pyrimidines were followed by UV spectroscopy in phosphate buffer (0.05M, $\mu=0.15$, 14.0 0.1°) at pH 7.1. See Table 8.

TABLE 8
Kinetic data for derivatives of cytosine and 5-fluorocytosine in pH 7.1 phosphate buffer (0.05 M, $\mu = 0.15$) at 24°

| Secondary amine | pKa | Half-live [SD (min)] Cytosine | 5-FC |
|---|---|---|---|
| Et | 10.98 | — 0.26(0.00) | XIV: 0.1 (0.0) |
| Me | 10.46 | X: 1.00(0.03) | XIII: 0.74(0.00 |
| Pi | 11.20 | VIII: 1.42(0.006) | XIIa: 0.89(0.03) XIIb: 0.90(0.01) |
| Py | 11.27 | —[a]: | XV: 1.05(0.01) |
| Mo | 8.36 | IXb: 9.72(0.04) | XVI: 9.10(0.20) |
| Pz | 9.82, 5.68 | XI: 27.19(0.30) | XVII: 26.30(1.00) |

[a]Derivative not synthesized with cytosine.

The hydrolyses were monitored at 268 nm for the cytosine derivatives and at 278 nm for 5-FC. These adducts exhibited a wide range of stabilities dependent upon the acidity of the parent compound, steric effects and the basicity of the secondary amine. The cytosine derivatives were more stable to hydrolysis than the corresponding 5-FC derivatives; i.e., increasing the acidity of the present drug (NH-acidic compound) increases the lability of these compounds. When looking at the adducts of a particular compound, increasing the steric effects of the secondary amine increased the rate of hydrolysis, with the diethylamino derivatives having the shortest half-lives. The basicity of the secondary amine also had an effect with the less acidic secondary amines—the morpholine adducts (IX and XVII) and the N-methylpiperazine adducts (XI and XVIII)—being more stable.

The hydrolysis of these compounds was also followed by ¹H NMR. A sample of derivative was dissolved in DMSO-d₆ and D₂O was added dropwise. The methylene protons at position 1 disappeared first, followed by the much slower disappearance of the N⁴-methylene protons—the reverse order of formation as would be expected from the principle of microscopic reversibility.

In an effort to elucidate the mechanism of hydrolysis for these compounds, the hydrolysis of the derivatives of 5-FC was also monitored in phosphate buffer (0.05M, $\mu=0.15$) at pH 6 and 8 (Table 9). The prodrugs were divided into 2 groups based on their rates of hydrolysis at basic pH. Compounds XIII, XVI and XVII hydrolyzed slower at basic pH, while the hydrolysis rates of compounds XV and XII were faster. These two groups can further be separated on the basis of the $pK_a$ of the secondary amine used to synthesize the derivative. Dimethylamine, morpholine and N-methylpiperazine all have pKₐs less than 11 while the pKₐs of piperidine and pyrrolidine are greater than 11. These data suggested two different, pH-dependent mechanisms of decomposition. At basic pH, the ability of the secondary amine to stabilize the incipient carbocation enhances the rate of decomposition. Therefore, the higher $pK_a$ amines were better able to donate the proton to the heteroatom at acidic pH than to stabilize the incipient carbocation formed at basic pH. For the adduct at the 1-position, the proton would be donated to the carbonyl group. At the N⁴-position, the proton would be transferred to the imino group at the 3-position. Both transfers could occur through a 6-membered intermediate. Regardless of the secondary amine used, when the hydrolysis was followed by $^1$H NMR, hydrolysis at the N$^4$-position was the rate-determining step.

TABLE 9

Half-lives of hydrolysis for selected 5-fluorocytosine derivatives in phosphate buffer (0.05 M, μ = 0.15) at 24°.

| Compound | Half-lives [± SD min)] | | |
|---|---|---|---|
| | pH 6.0 | pH 7.1 | pH 8.0 |
| XIII: Me | 0.51(0.03) | 0.74 | 0.87(0.02) |
| XV: Py | 1.01(0.03) | 1.05 | 0.66(0.02) |
| XIIb: Pi | 0.86(0.04) | 0.90 | 0.79(0.03) |
| XVI: Mo | 1.19(0.06) | 9.10 | 34.20(2.20) |
| XVII: Pz | 20.10(0.47) | 26.30 | 28.48(1.28) |

DETERMINATION OF LIPID AND AQUEOUS SOLUBILITIES

As expected, the adducts of 5-FC showed increased lipid solubility compared with that of the parent compound as measured in isopropyl myristate (IPM). The increase in lipid solubility accompanied the decrease in melting points (Table 10). The diethylaminomethyl derivative (XIV) was the most soluble in IPM, approximately 230 times more soluble than 5-FC, on a molar basis. The reversible N-alkylation removes sites of hydrogen-bonding, which lead to a decrease in the strong crystal lattice forces present in the parent compound. The relationship between melting point and solubility is exemplified by the two piperidine derivatives: the lower melting compound has a solubility in IPM twice that of the higher melting one.

The literature value for the aqueous solubility of 5-FC is 15 mg/ml (0.12M). This value was obtained by allowing a suspension of 5-FC in water to equilibrate for three hours and then analyzing the filtrate by UV spectroscopy; whereas in this case the water solubilities were determined after only a few minutes. Therefore, the water solubility of 5-FC reported here should be higher. It should be noted that it is not possible to get a true aqueous solubility for these derivatives since they decompose in water. But, in general, there was an increase in the apparent aqueous solubility realized with the derivatives. This combination of increased aqueous and lipid solubilities indicate improved topical delivery of 5-FC with the derivatives.

TABLE 10

Lipid and aqueous solubilities of 5-fluorocytosine and its N-Mannich base prodrugs

| Compound | Solubilities | | | |
|---|---|---|---|---|
| | IPM-(±SD) | | Water | |
| | mg/ml/× 10$^2$ | M(× 10$^4$) | mg/ml | M |
| 5-Fc | 0.50 (0.03) | 0.39 | 7 | 0.05 |
| XIV: Et | 271 (6.0) | 91 | >100 | >0.30 |
| XIII: Me | 23.0 (0.1) | 9.5 | >100 | >0.40 |
| XV: Py | 18.0 (0.3) | 6.1 | >100 | >0.30 |
| XIIa: Pi | 5.0 (0.9) | 1.6 | 10 | 0.03 |
| XIIb: | 12.0 (0.5) | 3.7 | 25 | 0.08 |
| XVI: Mo | 18.0 (0.7) | 3.5 | 25 | 0.08 |
| XVIII: Pz | 7.1 (0.5) | 2.2 | >100> | 0.30 |

DIFFUSION CELL EXPERIMENTS

First application

Hairless mouse skin was used to test the delivery of 5-FC and the derivatives through skin. 5-fluorocytosine and the prodrugs were applied as suspensions in the vehicle to the donor side of the diffusion cell. These suspensions (0.5 ml, 0.1M) were equivalent to 6.46 mg of 5-FC applied, except for the suspension used with the high-melting piperidine derivative (XIIa)—0.05M, 3.23 mg applied 5-FC. The fluxes were calculated as the rate of delivery of 5-FC through the skin (mg 5-FC/cm$^1$/h). The amounts of 5-FC left in the skin and donor phases were determined to obtain a mass balance; the mass balances were 90±5% of the applied dose. The donor phases were analyzed by $^1$H NMR at the end of the diffusion experiment, and the prodrugs were found to be intact by comparing the intensities of the 6-CH to the N—CH$_2$—N resonances.

The prodrugs were found to increase the delivery of 5-fluorocytosine. A biphasic delivery rate was seen for most of the compounds. The first phase is believed to be due to a shunt pathway through the hair follicles and sebaceous glands in the skin (Table 11). This initial phase lasted for 9 hours when 5-FC was delivered from IPM and 30 hours when 5-FC was delivered from PG. The initial phases for the prodrugs (in IPM) lasted approximately 9±3 hours. This transfollicular pathway has a lower resistance to diffusion. The second phase was attributed to the steady-state flux which continued for 27 hours for 5-FC in IPM and 18 hours for 5-FC in PG (Table 12). The steady-state phases (mg 5-FC/cm$^2$/h) for the delivery of 5-FC from the prodrugs lasted an average of 25±9 hours. The bis-N$^4$,1-dimethylaminomethyl-5-fluorocytosine prodrug gave the highest delivery rate of 5-FC, with a steady-state rate of delivery approximately 9 times that of 5-FC delivered from IPM. Although the two piperidinyl derivatives (XII) were applied at different suspension concentrations, their rates of delivery of 5-FC were the same (Table 12).

TABLE 11

Flux and permeability coefficient for initial phase of delivery of 5-fluorocytosine through hairless mouse skin

| Compound/Vehicle$^a$ | Flux(mg/cm$^2$/h) (± SD × 10$^3$) | K$_p$(cm/h) (× 10$^3$) | X-intercept (h) |
|---|---|---|---|
| 5-FC/PG | 1.41(0.02) | 0.013 | 1.2 |
| 5-FC/IPM | 3.03(1.46) | 67.3 | 2.4 |
| XVI: Mo/IPM | 5.25(0.55) | 73.9 | 2.8 |
| XVII: Pz/IPM | 4.80(3.38) | 67.3 | 2.8 |
| XIIa: Pi/IPM$^b$ | | | |
| XIIb: | 8.30(1.50) | 174 | 2.5 |
| XIII: Me/IPM | 18.2(6.2) | 149 | 2.5 |

$^a$Applied as suspensions of 0.1 M.
$^b$No initial phase seen, applied as suspension of 0.05 M.

TABLE 12

Flux and permeability coefficient for steady-state phase of delivery of 5-fluorocytosine through hairless mouse skin.

| Compound/Vehicle$^a$ | Flux(mg/cm$^2$/h) (± SD × 10$^3$) | K$_p$(cm/h) (× 10$^3$) | X-intercept (h) |
|---|---|---|---|
| 5-FC/PG | 2.57(0.81) | 0.24 | 13.1 |
| 5-FC/IPM | 5.0(1.5) | 111 | 6.0 |
| XVI: Mo/IPM | 15.10(0.97) | 213 | 9.9 |
| XVII: Pz/IPM | 26.1(8.41) | 919 | 14.2 |
| XIIa: Pi/IPM$^b$ | 34.6(19.9) | 1671 | 2.8 |
| XIIb: | 34.20(1.50) | 716 | 7.3 |
| XIII: Me/IPM | 44.7(2.7) | 365 | 4.7 |

$^a$Suspension of 0.1 M.
$^b$Suspension of 0.05 M.

There was a correlation between increased solubility in IPM and increased delivery of 5-FC. Though it may seem that increased solubility in the vehicle is causing the increase in delivery of 5-FC seen with the prodrugs, it is as probable that a concomitant increase in solubility in the skin is also responsible for the higher delivery rate, since the compound's ability to partition into the skin is the driving force for diffusion. If a drug's solubility in the vehicle is increased to the point that the vehicle competes with the skin for the drug, flux will be decreased. For example, while the solubility of 5-FC in propylene glycol (PG) is about 20 times greater than its solubility in IPM, the steady-state flux of 5-FC from PG is about one-half that of 5-FC from IPM. This illustrates a disadvantage of the formulation approach—only the solubility in the vehicle is affected (which also affects PC) and not the solubility in the skin. However, while these derivatives increase the solubility in the vehicle, they are probably also increasing the solubility in the skin. This is one advantage of using a prodrug to increase delivery into skin over a formulation approach—a prodrug can increase the compound's intrinsic solubility.

In addition to testing the prodrugs, several control experiments were performed (Table 13). In order to assess the stability of these prodrugs in sweat, a thin layer of sweat was swabbed on the skins prior to application of a 0.1M (0.5 ml) suspension of XIIb in IPM. Similarly, another set of skins was treated with sweat and 5-FC in IPM. The rates of delivery (mg 5-FC/cm$^2$/h) of 5-FC from both the prodrug and 5-FC were significantly increased (approximately 1.5 times) over the delivery rates obtained without sweat. An increase in the hydration state of the stratum corneum has been shown to increase the flux of compounds across the skin, so this result could have been expected. The prodrug seemed to remain intact in the presence of sweat since its rate of delivery of 5-FC was still approximately 7 times greater than that of 5-FC from IPM on skins treated in the same fashion: the same relative increase was seen in the absence of sweat.

The next experiment was an attempt to determine the effect of the paraformaldehyde and the secondary amine on the delivery of 5-FC through the skin, since amines have been reported to increase the percutaneous delivery of certain compounds. Paraformaldehyde and piperidine were allowed to react to form the aminomethylating agent and then 2 equivalents of the aminomethylating agent (neat) were added to 1 equivalent of 5-FC and the mixture was stirred for 48 hours in IPM. The resulting suspension (0.1M) was applied to the diffusion cells. The remaining suspension was filtered; and then the residue was washed with ether and analyzed by $^1$H NMR (DMSO-d$_6$). The data showed that the N-Mannich base derivative had formed. Therefore, the increased flux of 5-FC from this mixture could be due to N-Mannich base formation.

TABLE 13

| Compound/Vehicle | | Flux(mg/cm$^2$/h)[a] (± SD × 10$^3$) | X-intercept (h) |
|---|---|---|---|
| Control | | | |
| XIIb: | Pi/IPM | 8.30(1.5) | 2.4 |
| | | 34.2(1.6) | 6.0 |
| | 5-FC/IPM | 3.03(1.46) | 2.4 |
| | | 5.0(1.5) | 6.0 |
| Sweat study[b] | | | |
| XIIb: | Pi/IPM | 25.4(8.6) | 3.0 |
| | | 54.8(8.2) | 4.4 |
| | 5-FC/IPM | 4.4(1.0) | 2.3 |
| | | 8.2(0.6) | 5.9 |

TABLE 13-continued

Diffusion cell data for various controls compared to that for N$^4$, 1-(1'-piperidinyl)-methyl-5-flurocytosine (XIIB).

| Compound/Vehicle | Flux(mg/cm$^2$/h)[a] (± SD × 10$^3$) | X-intercept (h) |
|---|---|---|
| Effect of amime[c] | | |
| 5-FC + paraformaldehyde + piperidine/IPM | 7.8(4.3) | 3.0 |
| | 18.8(0.5) | 7.6 |

[a]Upper value is initial phase, lower value is steady-state flux.
[b]Sweat (donated by normal volunteer [KBS] was swabbed on the skins prior to application of 0.1 M suspension.
[c]Mixture of 0.1 mole of 5-FC and 0.2 moles of preformed aminomethylating agent.

Second application

In an effort to assess the effects of these compounds on the skin, a second application [theophylline in propylene glycol (Th/PG)] was performed in each diffusion cell experiment (Table 14). There was no initial phase seen with this system—only a steady-state flux (26±13 hours). The fluxes obtained from the second application were used as a measure of the impairment of the skin's barrier function. Several studies were performed to serve as baseline values. When the skins were allowed to leach for 120 hours (with no methanol wash), a flux of $1.41\pm0.09\times10^{-3}$ mg/cm$_2$/h for Th/PG was obtained. If the skin was washed with methanol 24 hours before application of Th/PG, the flux increased by slightly more than one-half. While the methanol wash does have some effect on the permeability of the skin, the wash is necessary to remove the donor phases after the first application. The remaining fluxes will be compared with this value. Application of IPM alone or 5-FC in IPM had the most detrimental effect on the skin, as shown by the large increases in the flux of Th/PG as compared with the controls (76 and 107 times, respectively). 5-Fluorocytosine itself seems to have an additive effect with IPM. The application of the aminomethylating agent (solution of paraformaldehyde and piperidine) in IPM seemed to have no significant effect compared with that of IPM—the flux of Th/PG in this experiment was not significantly different (p>0.10) from that seen after application of IPM alone. 5-Fluorocytosine in PG was the least detrimental combination tested, and this compares well with data obtained with other heterocyclic compounds. When the solublity parameter of a vehicle was within the range of 8 to 12 (cal/cm$^3$)$^{\frac{1}{2}}$ there was a significant increase in the flux of Th/PG in the second application. However, when the vehicles had a solubility parameter in the range of 12 to 18 (cal/cm$^3$)$^{\frac{1}{2}}$ there was much less of a perturbation of the skin's permeability. Porcine skin has been reported to have a solubility parameter of approximately 10 (cal/cm$^3$)$^{\frac{1}{2}}$, and the closer a vehicle's solubility parameter is to that of the skin, the more of an effect it should have on the skin. Isopropyl myristate has a solubility parameter of 8.5 (cal/cm$^3$)$^{\frac{1}{2}}$, while that of PG is 14.8. Since the solubility parameter of IPM is so close to that of the skin, it is possible that it is dissolving some of the constituents of the skin, such as the interstitial lipids of the stratum cornea. This has been shown to occur for certain lipid solvents, and could increase the permeability of the stratum corneum to polar drugs. Application of the prodrugs, except the piperidine adduct, caused significantly decreased fluxes of Th/PG when compared with those obtained after application of IPM or 5-FC in IPM (p>0.01); the piperidine derivative (XIIb) did not significantly change the flux over that obtained from IPM alone (p>0.10). While IPM does affect skin permeability, this alone did not account for the total increase in delivery of 5-FC into skin that was seen in the first applications. Also, IPM is a commonly used vehicle in pharmaceutical formulations and has been found to have a low potential for irritancy when applied to normal skin.

TABLE 14

Steady-state flux of theophylline from propylene glycol after application of 5-fluorocytosine and its N-Mannich base prodrugs (second application)

| First Application | Flux(mg/cm$^2$/h) (± SD × 10$^3$) | x-intercept (h) |
|---|---|---|
| Controls: | | |
| No methanol wash | 1.41(0.09) | 3.5 |
| Methanol wash | 2.42(0.14) | 4.7 |
| IPM | 184(23) | 1.6 |
| Aminomethylating agent/IPM$^a$ | 162(127) | 1.4 |
| Compound/Vehicle: | | |
| 5-FC/IPM | 261(5) | 1.0 |
| 5-FC/PG | 10.9(3.3) | 2.9 |
| XIII: Me/IPM | 81.3(15.3) | 1.0 |
| XIIb: Pi/IPM | 177(52) | 1.7 |
| XVI: Mo/IPM | 58.4(6 6) | 0.6 |
| XVIII: Pz/IPM | 76.6(10.2) | 1.0 |

$^a$Aminomethylating agent formed through the reaction of paraformaldehyde with piperidine.

EXPERIMENTAL AND CALCULATED SOLUBILITY PARAMETERS

The solubility of 5-FC was determined in a variety of vehicles (Table 15). According to the peak solubility method, 5-fluorocytosine's maximum solubility should occur in the vehicle that has the same (or closest) solubility parameter to that of 5-FC. A plot of $\ln(X_2)$ versus $(\delta_1 - \delta_2)^2$ was linear (r=0.978), therefore regular solution theory should describe the solubility of 5-FC in these solvents, and the solubility parameter of 5-FC should in the region of 14.8 to 16.5 (cal/cm$^3$)$^{\frac{1}{2}}$. The solubility parameter of 5-FC was also calculated using the group contribution method (Table 16). The calculated solubility parameter [16.5 (cal/cm$^3$)$^{\frac{1}{2}}$] was within the range predicted by the peak solubility method. The solubility parameters of the prodrugs were also calculated and compared with their steady-state rates of delivery of 5-FC from IPM (Table 17). Generally, as the solubility parameter of the prodrug approached that of skin [10 (cal/cm$^2$)$^{\frac{1}{2}}$] the delivery of 5-FC across the skin increased. Therefore, the solubility parameter of a compound could be used to predict the compound's ability to cross the skin, at least qualitatively. The closer the compound's solubility parameter is to that of skin, the larger its flux should be. Conversely, as the solubility parameter of a drug approaches that of the vehicle, its flux should decrease. At this point, the vehicle competes with the skin for drug thus decreasing the flux.

TABLE 15

Solubility of 5-fluorocytosine in various vehicles compared to solubility parameter of vehicle

| | Solubility of 5-FC | | | |
|---|---|---|---|---|
| Vehicle | mg/ml(± SD) | | mole fraction (× 10$^3$) | Solubility Parameter of vehicle (cal/cm$^3$)$^{\frac{1}{2}}$ |
| IPM | 0.0045 | (0.0003) | 0.01 | 8.3 |
| 1-octanol | 0.42 | (0.03) | 0.51 | 10.3 |
| DMF$^a$ | 3.52 | (0.17) | 211 | 12.1 |

TABLE 15-continued

Solubility of 5-fluorocytosine in various vehicles compared to solubility parameter of vehicle

| | Solubility of 5-FC | | | |
|---|---|---|---|---|
| Vehicle | mg/ml(± SD) | | mole fraction (× 10$^3$) | Solubility Parameter of vehicle (cal/cm$^3$)$^{\frac{1}{2}}$ |
| PG | 10.8 | (0.4) | 611 | 14.8 |
| EG$^b$ | 20.00 | (1.02) | 858 | 16.1 |
| EG:For(4:1) | 17.91 | (0.70) | 711 | 16.5 |
| EG:For(1:1) | 17.47 | (0.65) | 621 | 17.0$^c$ |
| For | 13.68 | (0.52) | 419 | 17.9$^c$ |

$^a$Dimethylformamide
$^b$Ethylene glycol
$^c$Calculated by taking the weighted average of the solubility parameters of the vehicles.
$^d$Formamide.

TABLE 16

Calculations of the solubility parameter of 5-fluorocytosine by the group contribution method

| Atom or Group | Number of Groups | $\Delta_{ei}$ (cal/mole) | | $\Delta_{vi}$ (cm$^3$/mole) | |
|---|---|---|---|---|---|
| C—O | 1 | | 4150 | | 10.8 |
| C— | 2 | 2 × 1030 | 2060 | 2 × (−5.5) | −11.0 |
| CH | 1 | | 820 | | −1.0 |
| F—C— | 1 | | −200 | | 4.0 |
| NH$_2$ | 1 | | 3000 | | 19.2 |
| —N— | 1 | | 2800 | | 5.0 |
| NH | 1 | | 1000 | | 4.5 |
| F | 1 | | 1000 | | 18.5 |
| Double bond | 2 | 2× 400 | 800 | 2×(−2.2) | −4.4 |
| Ring closure | 1 | | 250 | | 16.0 |

$\Sigma\Delta_{ei} = 16,680$  $\Sigma\Delta_{vi} = 61.1$
$\delta_i = (\Sigma\Delta\, e_i/\Sigma\Delta\, v_i)^{\frac{1}{2}} = 16.5$ (cal/cm$^3$)$^{\frac{1}{2}}$

TABLE 17

Comparison of solublity parameter with steady-state rate of delivery of 5-fluorocytosine

| Compound/ Vehicle | Solubility$^a$ Parameter(cal/cm$^3$)$^{\frac{1}{2}}$ | Flux(mg/cm$^2$/h) (× 10$^3$) |
|---|---|---|
| 5-FC/IPM | 16.5 | 5.0 |
| 5-FC/PG | 16.5 | 2.57 |
| XVI: Mo/IPM | 12.1 | 15.10 |
| XVIII: Pz/IPM | 11.5 | 26.1 |
| XIIb: Pi/IPM | 11.6 | 34.2 |
| XIII: Me/IPM | 11.6 | 44.7 |
| XIV: Et | 10.9 | —$^b$ |
| XV: Py | 12.0 | —$^b$ |

$^a$Calculated by group contribution method.
$^b$No diffusion cell experiments were performed with these compounds.

EXAMPLE 11

The following examples illustrate methods for preparing various derivatives of 5-iodo-2'-deoxycytidine (5-IDC) according to the invention and their effectiveness as prodrugs for enhanced delivery of 5-IDC across topical membranes:

SYNTHESIS

N$^4$-(1''-morpholinyl)methylcytidine monohydrate (XXI)

Amorphous solid, 93.7% yield; $^1$H NMR (DMSO-d$_6$) δ8.10–7.53 (m, 2, 6-CH and NH),5.88–5.55 (m, 2, 5-CH and anomeric H), 5.28–4.75 (m, 4, 2'- and 3' —CH—OH), 4.10 (d, 2, J×6 Hz, N—CH$_2$—N), 4.00–3.72 (m, 3, 4'—CH and 5'—CH$_2$), 3.72–3.48 (m, 5, $CH_2$—O—$CH_2$ and 5'—OH) and 2.70–2.22 (m, 4,$CH_2$—N—$CH_2$); UV ($CH_3CN$) max 275 nm ($\epsilon = 8.98 \times 10^3$ 1/mole) shoulder 245 nm ($\epsilon = 8.08 \times 10^3$ 1/mole), UV (HCl) max 305 nm ($\epsilon = 1.13 \times 10^4$ 1/mole) and UV (NaOH) max 275 nm ($\epsilon = 1.01 \times 10^4$ 1/mole) shoulder 245 nm ($\epsilon = 9.81 \times 10^3$ 1/mole). Anal: Calcd $C_{14}H_{22}N_4O_6$ $H_2O$: C, 46.66; H, 6.71. Found: C, 46.67; H, 6.80.

REACTION OF 5-IODO-2'-DEOXYCYTIDINE WITH FORMALDEHYDE AND A SECONDARY AMINE

To 0.33 g (0.004 mole) of 37% aqueous formaldehyde was added 0.004 mole of a secondary amine, and the solution was diluted to 10 ml with tetrahydrofuran. This solution was added to 0.35 g (0.001 mole) of 5-IDC. The solution was stirred for 1 to 2 days, and then it was triturated with ether 2 times. The oil that resulted was dried in a vacuum drying oven at 37° overnight to give the desired products:

$N^4$-(1''-piperidinyl)methyl-5-iodo-2'-deoxycytidine hydrate (XXIIa): Amorphous solid, 71% yield, IR (KBr) 3430 cm$^{-1}$ (M) (OH) and 1660 (S), 1630 (shoulder, M) and 1560 (M) (C=O and C=N); $^1$H NMR $\delta$8.40 and 8.33 (2s, 1, 6—CH), 6.97 (t, 1,J=6 Hz, NH, disappears in $D_2O$), 6.12 (t, 1,J=6 Hz, anomeric H), 5.33–4.97 (m, 2, 3'- and 5'—OH, disappears in $D_2O$)), 4.20 (m, 3, NH—$CH_2$—N and 3'—CH), 3.90–3.73 (m,1, 4'—CH), 3.73–3.53 (m, 2, 5'—$CH_2$), 2.63–2.33 (s, 4, $CH_2$—N—$CH_2$), 2.27–2.08 (m, 2, 2'13 $CH_2$) and 1.67–1.27 (s, 6, $CH_2$—$CH_2$); UV ($CH_3CN$) max 296 nm ($\epsilon = 5.57 \times 10^3$ 1/mole) shoulder 254 nm ($\epsilon = 5.25 \times 10^3$ 1/mole), UV (HCl) 313 nm ($\epsilon = 8.64 \times 10^3$ 1/mole) and UV (NaOH) max 296 nm ($\epsilon = 5.34 \times 10^3$ 1/mole) shoulder 254 ($\epsilon = 5.21 \times 10^3$ 1/mole).

Anal. Calcd for $C_{15}H_{23}IN_4O_4$ 0.5 $H_2O$: C, 39.23; H, 5.26. Found: C, 39.22; H, 5.11.

$N^4$-(1''-morpholinyl)methyl-5-iodo-2'-deoxycytidine hydrate (XXIIIa): Amorphous, hygroscopic solid, 74% yield, $^1$H NMR (DMSO-$d_6$) $\delta$8.34–8.30 (2s, 1, 6—CH), 7.10 (t, 1, J=6 Hz, NH, disappears in $D_2O$), 6.10 (t, 1, J=6 Hz, anomeric H), 5.30–4.93 (m, 2, 3'- and 5'—OH, disappear in $D_2O$), 4.40–4.00 (m, 3, 3'—CH and NH—$CH_2$—N, collapses to singlet in $D_2O$), 4.07–3.40 (m, 6, $CH_2$—N—$CH_2$ and 5'—$CH_2$), 2.63–2.33 (s, 4, $CH_2$—O—$CH_2$) and 2.23–1.93 (m, 2, 2'—$CH_2$); UV ($CH_3CN$) max 296 nm ($\epsilon = 5.38 \times 10^3$ 1/mole) shoulder 255 nm ($\epsilon = 5.39 \times 10^3$ 1/mole), UV (HCl) max 313 nm ($\epsilon = 7.21 \times 10^3$ 1/mole) and UV (NaOH) max 296 nm ($\epsilon = 5.30 \times 10^3$ 1/mole) shoulder 255 nm ($\epsilon = 5.32 \times 10^3$ 1/mole).

Anal. Calcd for $C_{14}H_{21}IN_4O_5$ $H_2O$; C, 35.76; H, 4.93. Found: C, 35.76; H, 5.12.

REACTION OF 5-IODO-2'-DEOXYCYTIDINE WITH PARAFORMALDEHYDE AND A SECONDARY AMINE

To 0.12 g (0.004 mole) of paraformaldehyde in 20 ml of methylene chloride was added 0.004 mole of a secondary amine and the suspension was stirred overnight. The solution that resulted was concentrated and the residue was diluted with 10 ml of tetrahydrofuran. The solution was added to 0.35 g (0.001 mole) of 5-iodo-2'-deoxycytidine. The suspension was stirred overnight. The solution that resulted was concentrated, and the residue was triturated twice with ether and then a mixture of ether and petroleum ether (1:1). The solid was filtered, and dried under vacuum with potassium hydroxide pellets as a desiccant to give the desired products:

$N^4$-(1''-piperidinyl)methyl-5-iodo-2'-deoxycytidine hydrate (XXIIb): hygroscopic solid, 68% yield, spectral data same as XXIIa, $R_f$(ether: methanol [1:1]) 0.26.

Anal. Calcd for $C_{15}H_{23}IN_4O_4$ 0.5 $H_2O$: C, 39.23; H, 5.26; N, 12.20. Found: C, 39.24; H, 5.27; N, 12.09.

$N^4$-(1''-morpholinyl)methyl-5-iodo-2'-deoxycytidine hydrate (XXIIIb): hygroscopic solid, 84% yield, spectral data same as XXIIIa. (See Table 18.)

TABLE 18

Structures of the derivatives of cytidine and 5-iodo-2'-deoxycytidine

| R = [a] | Cytidine (X = H; R' = OH) | 5-IDC (X = I; R' = H) |
|---|---|---|
| —N($C_2H_5$)$_2$(Et) | XIX | — |
| —N (Pi) (piperidinyl ring) | XX | XXIIa, |
| —N O (Mo) (morpholinyl ring) | XXI | XXIIIa, |

[a]Compounds are identified hereafter by number and by the abbreviation for the secondary amine.

MEASUREMENT OF HALF-LIVES AND RATES OF HYDROLYSIS

The hydrolysis of the prodrugs in pH 7.1 buffer (0.05M, =0.15) was monitored by UV spectroscopy at 294 nm, by measuring the appearance of 5-IDC. A plot of log ($A_t - A_\infty$) versus time was linear so first-order reaction kinetics were assumed. Each hydrolysis was performed in triplicate at a constant temperature of 24.0°±0.1° and the half-lives and rates of hydrolysis were obtained using the Guggenheim method. Stock solutions of the prodrugs were made in dry acetonitrile, and 0.1 ml of the solution was added to 3 ml of buffer in a cuvette. The final concentation in the cuvette was between 10$^4$ and 10$^5$M. The acetonitrile did not affect the pH of the buffer. The pH of the solution in cuvettes were checked after the hydrolyses were completed and were found to have remained constant.

DETERMINATION OF LIPID AND AQUEOUS SOLUBILITIES

The lipid solubilities of 5-iodo-2'-deoxycytidine and its N-Mannich base prodrugs were determined in isopropyl myristate. Three suspensions of the drug or prodrugs were stirred for 48 hours and then filtered. The filtrates were then diluted with either methanol, for the parent drug or dry acetonitrile, for the N-Mannich base prodrugs. The concentration of compound in solution was determined by monitoring the UV absorption at 294 nm ($\epsilon=5.79\times10^3$ 1/mole) for 5-IDC, 333 nm ($\epsilon=2.46\times10^4$) for the formamidine derivative and 296 nm for the derivatives. The aqueous solubilities were obtained as described above.

DIFFUSION CELL EXPERIMENTS

Diffusion experiments were performed in triplicate for each compound tested as described above. The skins of female hairless mice were obtained and secured to the diffusion cells with the dermis in contact with the receptor phase. The receptor phase contained isotonic phosphate buffer at pH 7.3 (32°) with 0.1% formaldehyde to inhibit microbial growth. The receptor phase was kept at a constant temperature of 32° and was stirred magnetically.

The skins were placed in contact with the receptor for 48 hours to remove any water soluble, UV-absorbing compounds. The receptor phases were changed three times. The donor phases were applied as suspensions (0.5 ml, 0.05M) to the skin surface. The suspensions were stirred for 48 hours prior to application. Samples (3 ml) were removed from the receptor phases at 3, 6, 9, 12, 18, 21, 24, 30, 36 and 48 hours after application of the donor phases. Each sample was replaced by an equal amount of fresh buffer. Each sample was filtered (0.45 µm membrane filter) and the samples were analyzed by HPLC using a fixed-wavelength UV detector at 280 nm. A Dupont Zorbax ODS (4.6×250 mm) reverse-phase column was used with a mobile phase of 13% acetonitrile in water at a flow rate of 1.0 ml/min. Fifty microliters of the sample was injected onto the column. The retention time of 5-IDC in this system was 5 min. Calibration curves (r=0.9989, n=7) of peak area (mm$^2$) versus concentration were used to quantify the concentration of 5-IDC in the samples. The cumulative amount of 5-IDC in the receptor phase was calculated as described for 5-FC. In order to detect the formation of 5-IDU, samples at times 3, 9 and 48 hours were also tested using a mobile phase of 12% tetrahydrofuran in water.

After the 48 hours, the remaining donor phase was removed by washing the skin surface with 20 ml of methanol. The washings were combined, diluted to 200 ml with methanol and analyzed by UV (294 nm, $\epsilon=5.79\times10^3$ 1/mole) to determine the amount of 5-IDC remaining in the donor phases. The receptor phases were then replaced with fresh buffer and the skins were allowed to remain in contact with the buffer for an additional 24 hours. The receptor phase was then sampled and analyzed by HPLC to determine the amount to 5-IDC left in the skin. These last two steps were used to determine the mass balance. This part of the diffusion cell experiment is referred to as the first application.

After this last sampling, the receptor phase was again changed. The skins were left in contact with the receptor phases for 30 minutes and then a 3 ml sample was taken and analyzed for 5-IDC to measure the 5-IDC that had been leached from the skins. A suspension of theophylline in PG (Th/PG; 0.5 ml, 0.4M) was then applied to each diffusion cell. Samples (3 ml) were removed at 3, 6, 9, 12, 24 and 48 hours after application of Th/PG. The UV absorbances of the samples was monitored at 270 nm ($\epsilon=1.02\times10^4$ 1/mole). This phase of the diffusion cell experiment is labelled the second application. Student's t-test (one-tailed) was used to test for significant differences between the fluxes (Sloan et al, Int. J. Pharm., 12, 299–313 (1982)).

For each diffusion cell experiment, the cumulative amount of 5-IDC (mg) found in the receptor phase was plotted versus the sample time. The slopes for each phase of the plotted lines were obtained by linear regression analysis; the slopes were then divided by the surface area of the diffusion cells (4.9 cm$^2$) to obtain a value for flux (J) in mg/cm$^2$/h. The reported fluxes are the average flux for the three cells.

EXPERIMENTAL AND CALCULATED SOLUBILITY PARAMETERS

The solubility of 5-IDC was determined in the following solvents: 1-octanol, 1-propanol, propylene glycol, ethylene glycol and formamide. The mole fraction solubilities were then used to determine the solubility parameter of 5-IDC by the peak solubility method. The solubility parameters of 5-IDC and its N-Mannich bases were also calculated using the group contribution method of Fedors (Fedors, Polym. Eng. Sci., 14, 472 (1974).

In these nucleosides there were two possible sites of alkylation possible—at the 3-position and on the exocyclic amino group ($N^4$). The reaction of formaldehyde with nucleosides and nucleic acids has been well documented. McGhee studied the reaction of formaldehyde with cytidine and isolated and characterized the $N^4$-hydroxymethyl derivative by $^1$H NMR. See McGhee et al, supra. Due to the larger number of protons, the $^1$H NMR spectra of these derivatives were not as definitive as those obtained for the N-Mannich base derivatives of the pyrimidine bases themselves, but there was only one peak that corresponded to the N—CH$_2$—N group. When the UV absorptions were compared with those of various monosubstituted cytidines, the UV absorptions more closely resembled those of an $N^4$-substituted cytidine. Therefore, the N-Mannich base derivatives of cytidine and 5-IDC were assigned to the $N^4$-position.

HYDROLYSIS DATA

The hydrolysis of the piperidinyl (XXII) and morpholinyl (XXIII) adducts of 5-IDC was monitored in pH 7.1 buffer at 24°. The half-life ($t_{\frac{1}{2}}$) of XXIIb was 0.89 ±0.06 min; the $t_{\frac{1}{2}}$ of XXIIIb was 12.8 ±0.6 min. As seen with the 5-FC adducts, the morpholine derivative was more stable than the piperidine derivative at this pH. Since these adducts were substituted at the $N^4$-position, and the rate-determining step for decomposition for the 5-FC adducts was hydrolysis at the $N^4$-position, these adducts were expected to decompose by the same mechanism proposed above.

SOLUBILITY DETERMINATIONS.

The derivatives showed a significant increase in lipid solubility compared with that of 5-IDC (Table 19). Since these prodrugs are unstable in protic solvents, IPM was also used as the vehicle to test these derivatives in the diffusion cells. There was a significant difference in the lipid solubilities of XXIIa and XXIIb (p>0.025), this could be due to differences in the method of synthesis.

While it is not possible to obtain a true water solubility for these compounds, the apparent water solubility of 5-IDC was increased through the N-Mannich bases (Table 19).

TABLE 19
Lipid and aqueous solubilities of 5-iodo-2'-deoxycytidine and its N-Mannich base prodrugs

| Compound | IPM (±SD) mg/ml(× $10^2$) | M(× $10^5$) | Water mg/ml | M(× $10^3$) |
|---|---|---|---|---|
| 5-IDC | 0 | 0 | <1 | <2.8 |
| XXIIa: Pi | 2.8(0.3)[a] | 6.2 | 100 | 222 |
| XXIIb: | 1.6(0.5)[a] | 3.6 | 100 | 222 |
| XXIIIb: Mo | 1.3(0.8) | 2.9 | 20 | 44 |

[a]Significantly different from each other, p>0.025.

DIFFUSION CELL EXPERIMENTS

First application

The topical delivery of 5-IDC from the piperidinyl adduct (XXIIa) and from 5-IDC in IPM was tested with hairless mouse skin. Suspensions (0.05 M, 0.5 ml) were applied in order to keep a constant driving force for diffusion. Since 5-IDC can be deaminated to 5-iodo-2'-deoxyuridine (5-IDU) (which is also active as an antiviral agent) by mammalian deaminases, it was necessary to determine if this conversion had occurred in the diffusion cell system. A mobile phase of 12% tetrahydrofuran in water was found to separate 5-IDU from 5-IDC on a Dupont Zorbax ODS column (4.6×250 mm), but could not be used to quantify the 5-IDC since there was no separation of 5-IDC from the solvent front. With this system, no conversion of 5-IDC to 5IDU was detected in the diffusion cells. While some deaminase activity is present in hairless mouse skin, it is known that the responsible enzymes leach out of the skin.

A mobile phase of 13% acetonitrile in water was used with a Dupont Zorbax ODS (4.6×250 mm) at a flow rate of 1.0 ml/min to determine the amount of 5-IDC in the receptor phase; the retention time for 5-IDC was 5 min. A UV detector at a fixed wavelength of 280 nm was used. External calibration using peak area ($mm^2$) was used to determine the concentration of 5-IDC in the samples. The mass balances were approximately 91% of the applied dose (8.83 mg as 5-IDC). Once again, a biphasic delivery rate was seen. The initial phase was attributed to transfollicular transport (shunt pathway) into the skin (Table 20). This initial phase lasted for 19 hours when 5-IDC was delivered from IPM, but only for 6 hours when 5-IDC was delivered from the prodrug in IPM. The steady-state flux of 5-IDC from XXIIa was approximately twice that of 5-IDC from IPM (Table 20). Also, the steady-state delivery of 5-IDC from XXIIa lasted longer (18 hours) than that from 5-IDC in IPM (11 hours), the steady-state rate of delivery had a faster onset for the prodrug as well.

Second application

Theophylline (0.4 M) in propylene glycol was applied to the skins in order to assess the effect of the first application on the permeability of the skins (Table 20). Propylene glycol was used to deliver the theophylline since its effect on skin permeability is minimal. While IPM does have an effect on skin permeability, the prodrugs are stable in it (by $^1$H NMR). 5-Iodo-2'-deoxycytidine had the greatest effect on skin permeability, with the flux of theophylline from PG increasing 1.3 times. The flux of theophylline in PG after application of the prodrug was not significantly different from that of IPM alone (p>0.10).

TABLE 20
Diffusion cell data for 5-iodo-2'-deoxycytidine and its N-Mannich base prodrug in IPM and the second application of theophylline in PG (Th/PG).

FIRST APPLICATION

| Compound/IPM[b] | Flux(mg/$cm^2$/h)[a] (±SD × $10^3$) | X-intercept (h) |
|---|---|---|
| 5-IDC | 2.2 (0.7) | 5.0 |
| | 5.8 (1.3) | 14.0 |
| XXIIa: Pi | 3.3 (3.3) | 2.9 |
| | 13.5 (4.1) | 5.3 |

SECOND APPLICATION (Th/PG)

| First Application | Flux(mg/$cm^2$/h)[c] (±SD × $10^3$) | X-intercept (h) |
|---|---|---|
| Methanol wash[d] | 2.42(0.14) | 4.7 |
| IPM | 184 (23)) | 1.6 |
| 5-IDC/IPM | 246 (17) | 0.6 |
| XXIIa: Pi/IPM | 192 (38)[e] | 1.0 |

[a]Upper value is initial phase, lower value is steady-state flux.
[b]Applied as 0.05 M suspensions.
[c]Applied as 0.4 M suspension.
[d]No first application, skins washed with methanol before application of Th/PG.
[e]Not significantly different from flux after first application of IPM.

EXPERIMENTAL AND CALCULATED SOLUBILITY PARAMETERS

The solubility of 5-IDC was determined in different vehicles as described above (Table 21). The maximum solubility occurred in formamidine and this solvent has the highest solubility parameter of any solvent compatible with these studies. A graph of $\ln(X_2)$ versus $(\delta_1-\delta_2)^2$ was linear (r=0.995); therefore, application of regular solution theory is valid for these solutions. The solubility parameters of 5-IDC and its prodrugs were calculated using a group contribution method. By this method, the solubility parameter for 5-IDC was 17.2 $(cal/cm^3)^{\frac{1}{2}}$, which is comparable with that of formamide (Table 22). The solubility parameters of the piperdinyl and morpholinyl derivatives were 14.5 and 15.3 $(cal/cm^3)^{\frac{1}{2}}$, respectively. As found with the 5-FC prodrugs, as the solubility parameter of the prodrug approaches that of the skin, the delivery of the parent drug into the skin increases.

TABLE 21
Solubility of 5-iodo-2'-deoxycytidine in various vehicles compared to the solubility parameter of vehicle

| Vehicle | Solubility of 5-IDC mg/ml(±SD) | mole fraction (× $10^3$) | Solubility Parameter of vehicle $(cal/cm^3)^{\frac{1}{2}}$ |
|---|---|---|---|
| IPM | 0 | 0 | 8.5 |
| 1-octanol | 0.34 (0.03) | 0.96 | 10.3 |
| 1-propanol | 2.15 (0.18) | 6.09 | 12.0 |
| PG[a] | 19.67 (0.34) | 55.7 | 14.8 |
| EG[b] | 31.53 (0.79) | 89.2 | 16.1 |
| For | 56.92 (1.86) | 161 | 17.9 |

[a]Ethylene glycol.
[b]Formamide.

TABLE 22
Calculation of the solubility parameter of 5-iodo-2'-deoxycytidine by the group contribution method

| Atom or Group | Number of Groups | $\Sigma\Delta e_1$ (cal/mole) | $\Sigma\Delta v_1$ ($cm^3$/mole) |
|---|---|---|---|
| C=0 | 1 | 4150 | 10.8 |
| C= | 2 | 2 × 1030  2060 | 2 ×(−5.5)  −11.0 |

TABLE 22-continued

Calculation of the solubility parameter of
5-iodo-2'-deoxycytidine by the group contribution method

| Atom or Group | Number of Groups | $\Sigma \Delta e_i$ (cal/mole) | | $\Sigma \Delta v_i$ (cm³/mole) | |
|---|---|---|---|---|---|
| CH | 4 | 4 × 820 | 3280 | 4 × (−1.0) | −4.0 |
| CH₂ | 2 | 2 × 1180 | 2360 | 2 × 16.1 | 32.2 |
| I—C = | 1 | | −910 | | 4.0 |
| NH₂ | 1 | | 3000 | | 19.2 |
| —N = | 1 | | 2800 | | 5.0 |
| N | 1 | | 1000 | | −9.0 |
| I | 1 | | 4550 | | 31.5 |
| OH | 2 | 2 × 7120 | 14240 | 2 × 10.0 | 20.0 |
| O | 1 | | 800 | | 3.8 |
| Double bond | 2 | 2 × 400 | 800 | 2×(−2.2) | −4.4 |
| Ring closure | 2 | 2 × 250 | 500 | 2 × 16.0 | 32.0 |

$\Sigma \Delta e_i = 38,630 \quad \Sigma \Delta v_i = 130.1$
$\delta_i = (\Sigma \Delta e_i / \Sigma \Delta v_i)^{\frac{1}{2}} = 17.2 \ (cal/cm^3)^{\frac{1}{2}}$

What is claimed is:

1. A compound of the formula:

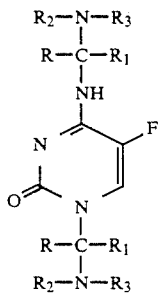

wherein:
R and R₁ may be the same or different and are selected from the group consisting of H; cycloalkyl groups having up to 10 carbon atoms; or straight or branched chain alkyl, alkenyl or alkynyl of 1 to 10 carbon atoms;
R₂ and R₃ together with the nitrogen atom to which they are bonded form a pyrrolidine, piperidine, N-methyl piperazine, piperazine or morpholine ring;
or a non-toxic pharmaceutically acceptable salt, adduct, oxide or metal complex thereof.

2. A compound according to claim 1, bis-N⁴,1-(dimethylamino)methyl-5-fluorocytosine.

3. A pharmaceutical composition in unit dosage form adapted for topical administration to a human or nonhuman animal in need thereof comprising a biologically effective amount of a compound of the formula:

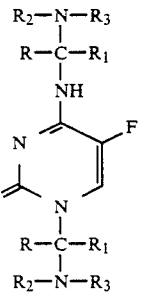

wherein:
R and R₁ may be the same or different and are selected from the group consisting of H; cycloalkyl groups having up to 10 carbon atoms; or straight or branched chain alkyl, alkenyl or alkynyl of 1 to 10 carbon atoms;
R₂ and R₃ together with the nitrogen atom to which they are bonded form a pyrrolidine, piperidine, N-methyl piperazine, piperazine or morpholine ring;
or a non-toxic pharmaceutically acceptable salt, adduct, oxide or metal complex thereof and a pharmaceutically acceptable, topically administrable carrier therefor, said aminomethyl derivative having an enhanced delivery across topical membranes of said animal upon topical application as compared with said underivatized biologically active substance and being capable of exerting said biological activity after delivery across said topical membrane.

4. A pharmaceutical composition according to claim 3 wherein said derivative is bis-N⁴,1-(dimethyl-amino)-methyl-5-fluorocytosine.

5. A method of administering a biologically active substance to a human or non-human animal in need thereof comprising topically applying to said animal a biologically effective amount of an aminomethyl derivative of a biologically active substance having the formula set forth in claim 3 or a non-toxic pharmaceutically acceptable salt, adduct, oxide or metal complex thereof and a pharmaceutically acceptable, topically administrable carrier therefor, said aminomethyl derivative having an enhanced delivery across topical membranes of said animal upon topical application as compared with said underivatized biologically active substance and being capable of exerting said biological activity after delivery across said topical membrane.

6. A method according to claim 5 wherein said derivative is bis-N⁴,1-(dimethylamino)methyl-5-fluoro-cytosine.

* * * * *